United States Patent
Bohde

(10) Patent No.: US 12,097,458 B2
(45) Date of Patent: Sep. 24, 2024

(54) MOLD AND FUNGAL (MYCOTOXIN) TOXIN REMEDIATION

(71) Applicant: John Bohde, Naples, FL (US)

(72) Inventor: John Bohde, Naples, FL (US)

( * ) Notice: Subject to any disclaimer, the term of this patent is extended or adjusted under 35 U.S.C. 154(b) by 0 days.

(21) Appl. No.: 17/314,709

(22) Filed: May 7, 2021

(65) Prior Publication Data
US 2022/0040623 A1 Feb. 10, 2022

Related U.S. Application Data

(60) Provisional application No. 63/062,614, filed on Aug. 7, 2020.

(51) Int. Cl.
| | | |
|---|---|---|
| *B01D 46/10* | (2006.01) | |
| *A47L 9/10* | (2006.01) | |
| *A47L 9/12* | (2006.01) | |
| *B08B 1/10* | (2024.01) | |
| *C11D 3/386* | (2006.01) | |

(52) U.S. Cl.
CPC .............. *B01D 46/10* (2013.01); *A47L 9/102* (2013.01); *A47L 9/12* (2013.01); *B08B 1/10* (2024.01); *C11D 3/386* (2013.01)

(58) Field of Classification Search
CPC . B01D 46/10; A47L 9/102; A47L 9/12; B08B 1/001; C11D 3/386; C11D 3/0047; C11D 3/188; C11D 11/0052; C11D 3/2044; C11D 3/48; A61L 2/18; E04G 23/0296
See application file for complete search history.

(56) References Cited

U.S. PATENT DOCUMENTS 5,768,907 A * 6/1998 Lee .................. A01M 1/24
43/132.1
6,131,237 A * 10/2000 Kasper ............... A47L 5/30
15/320

(Continued)

OTHER PUBLICATIONS

Twin Home Experts, What Do Mold Professionals Use to Kill Mold, Aug. 31, 2019, https://www.youtube.com/watch?v=uDyUB2qENJA (Year: 2019).*

*Primary Examiner* — Dung H Bui
(74) *Attorney, Agent, or Firm* — Blake E. Vande Garde; AVEK IP, LLC

(57) ABSTRACT

A method of treating a building for mold contamination including the steps of assessing and locating mold growth areas, constructing a containment barrier around the mold growth areas, vacuuming, abrading and surface treating the mold growth areas, ceilings, walls and window treatments with mold cleaner, replacing air filters from air handlers, removing all registers and vent grills in the treated areas and washing the vent grills with mold cleaner, vacuuming all registers and accessible ductwork, treating the heating and ventilation system, associated ductwork and wall cavities with an atomized mold cleaner, vacuuming all flooring, horizontal surfaces, walls, furniture and mattresses, re-vacuuming all flooring, re-treating the heating and ventilation system and associated ductwork with an atomized mold cleaner and re-treating the work area including any exposed wall cavities with an atomized mold cleaner, deconstructing and discarding containment barrier and reinstalling all registers and vent grills.

16 Claims, 5 Drawing Sheets

(56) References Cited

U.S. PATENT DOCUMENTS

| | | | | |
|---|---|---|---|---|
| 6,576,604 B1* | 6/2003 | Hoshino | C11D 3/38654 | 510/438 |
| 7,357,831 B2* | 4/2008 | Dancey | F24F 11/875 | 55/318 |
| 7,407,624 B2* | 8/2008 | Cumberland | A61L 9/015 | 422/123 |
| 7,690,148 B2* | 4/2010 | Hedman | A01M 1/2094 | 43/132.1 |
| 7,837,932 B2* | 11/2010 | Hedman | A01M 1/2094 | 43/132.1 |
| 7,902,140 B1* | 3/2011 | Hansen | C11D 3/43 | 510/480 |
| 8,221,678 B2* | 7/2012 | Hedman | A61L 2/16 | 422/1 |
| 8,272,143 B1* | 9/2012 | Hedman | A61L 2/10 | 422/1 |
| 2002/0182184 A1* | 12/2002 | Pearl | C11D 3/386 | 424/94.4 |
| 2002/0189154 A1* | 12/2002 | Hedman | A01M 19/00 | 43/132.1 |
| 2003/0152481 A1* | 8/2003 | Birnecker | A61L 2/22 | 422/1 |
| 2004/0023823 A1* | 2/2004 | Itoh | C11D 3/2006 | 510/463 |
| 2004/0091390 A1* | 5/2004 | Bentley | A61L 2/18 | 405/32 |
| 2004/0198625 A1* | 10/2004 | Mckechnie | C11D 3/0063 | 510/302 |
| 2005/0013727 A1* | 1/2005 | Hedman | A61L 9/16 | 422/26 |
| 2005/0220662 A1* | 10/2005 | Hedman | F23G 7/06 | 422/1 |
| 2007/0014687 A1* | 1/2007 | Tabor | A61L 2/18 | 424/275.1 |
| 2007/0105741 A1* | 5/2007 | Bowker | A61K 8/922 | 510/462 |
| 2007/0110780 A1* | 5/2007 | Gorton | A01N 65/00 | 424/754 |
| 2011/0064605 A1* | 3/2011 | Hedman | A01M 1/2094 | 422/1 |
| 2013/0116162 A1* | 5/2013 | Armstrong | C11D 17/0021 | 510/501 |
| 2015/0305320 A1* | 10/2015 | Hedman | A01M 1/24 | 43/132.1 |
| 2016/0114349 A1* | 4/2016 | Bush | C11D 11/0023 | 401/143 |
| 2017/0304874 A1* | 10/2017 | Hennigan | C11D 3/2003 | |
| 2018/0242577 A1* | 8/2018 | Tsai | A01N 25/34 | |
| 2018/0332855 A1* | 11/2018 | Arafat | A61L 2/18 | |
| 2018/0340733 A1* | 11/2018 | Blais | F26B 21/001 | |
| 2018/0353631 A1* | 12/2018 | Grinstead | A61L 2/183 | |
| 2019/0167829 A1* | 6/2019 | Grinstead | A61L 2/085 | |
| 2019/0209487 A1* | 7/2019 | Anastassov | A61K 31/352 | |
| 2019/0255205 A1* | 8/2019 | Cosman | F26B 21/001 | |
| 2019/0321867 A1* | 10/2019 | Bates | A47L 13/17 | |
| 2019/0382693 A1* | 12/2019 | St. Peter | C11D 17/0013 | |
| 2020/0138034 A1* | 5/2020 | Macnaughtan | A01N 59/00 | |
| 2020/0190446 A1* | 6/2020 | Sivik | C11D 1/00 | |
| 2020/0253203 A1* | 8/2020 | Sehgal | C11D 3/3769 | |

* cited by examiner

Figure 8

MOLD AND FUNGAL (MYCOTOXIN) TOXIN REMEDIATION

FIELD OF INVENTION

The present invention relates to compositions suited for treating and inhibiting microbial growth and fungal toxin infestation on building materials, including materials used in the construction of residential and commercial properties. The present invention further relates to a mold cleaning system, a method of making antimicrobial compositions, and to methods of applying the antimicrobial compositions to building material surfaces.

BACKGROUND OF THE INVENTION

All molds are a large and taxonomically diverse number of the fungi family. Fungi include mold, mildew, yeasts, smuts, crop rusts, slimes, and mushrooms. The fungi kingdom includes a plurality of beneficial organisms, in terms of both their ecological and economic roles. Fungi are the principal decomposers of dead organic material in ecological systems. Additionally, there are plants that grow due to a symbiotic fungus that inhabit their roots and supply essential nutrients to the plants. Some fungi provide drugs such as antibiotics, while others provide foods to eat, including cheese, mushrooms, truffles, and morels. Single celled fungi are responsible for alcohol production and the bubbles in bread, champagne, and beer.

Molds grow naturally in the environment. They can be found anywhere you look, even inside a building. While there are over 100,000 species of mold worldwide, there are only about 1,000 species in the United States. Fungi are adaptable and can change in form and function depending on a variety of factors. For instance, some mold species are generally non-toxic, however, when their space is invaded by a competing fungi species, these non-toxic molds can become toxic. They will produce toxins in order to kill or dissuade invaders. Unfortunately, molds also create many challenges for humans.

Molds are pervasive around the entire world. Molds thrive in high mountainous terrain as well as in caves deep within the Earth. Molds can survive in anaerobic environments and in freezing or scorching environments. Molds thrive and flourish in the comfort zone temperature range for humans and beyond.

Unfortunately, the presence of mold can also present health issues for humans. More specifically, molds found in dwellings and office buildings are responsible for health problems that range from itching eyes, sneezing, and coughing to serious allergic reactions, asthma attacks, bleeding lungs, and even death. Research has shown that million cases of asthma may be attributed to dampness and mold exposure in the home, schools, offices, and other buildings, costing taxpayers billions annually in lost work and productivity. Additionally, people spend billions of dollars every year on healthcare visits and prescription medications to treat the symptoms resulting from mold exposure.

Mold grows on nearly any surface as long as it has oxygen, moisture, and an organic food source. Molds reproduce by creating spores which constantly float through the air, looking for a damp dark place to settle and grow. Mold spores and mycotoxins affect human health when levels reach a threshold. Exposure to spores and mycotoxins can cause irritation and allergic response upon contact, as well as other serious symptoms and diseases. Spores can be irritants and cause allergic reactions both on the surface of the skin and inside the human body. They can grow inside nasal passages, sinus cavities, bronchial passages, and lungs, living on a combination of particulate matter, mucus, and tissue. Even dead mold spores can produce irritation, allergic reactions, and other health problems. Some mold species appear to produce only one toxin, while others are known to produce over one hundred. Some molds also produce compounds called synergizers, which enhance the effects of their toxins. When an individual smells mold, that individual and those around them are breathing microbial volatile organic compounds (MVOCs) produced by mold, which may be toxic. More than five hundred MVOCs produced by mold species have been identified so far.

Mycotoxins are a toxic secondary metabolite produced by organisms of the fungus kingdom capable of causing disease and death in both humans and other animals. Examples of mycotoxins causing human and animal illness include aflatoxin, citrinin, fumonisins, ochratoxin A, patulin, trichothecenes, zearalenone, and ergot alkaloids such as ergotamine. One mold species may produce many different mycotoxins, and several species may produce the same mycotoxin. Buildings are a source of mycotoxins and people living or working in areas with mold increase their chances of adverse health effects. Molds growing in buildings can be divided into three groups being primary, secondary, and tertiary colonizers. Each group is categorized by the ability to grow at a certain water activity requirement.

Mycotoxicosis refers to the poisoning associated with exposures to mycotoxins. Mycotoxins have the potential for both acute and chronic health effects via ingestion, skin contact, inhalation, and entering the blood stream and lymphatic system. They inhibit protein synthesis, damage macrophage systems, inhibit particle clearance of the lung, and increase sensitivity to bacterial endotoxin. The symptoms of mycotoxicosis depend on the type of mycotoxin, the concentration and length of exposure, as well as age, health, and sex of the exposed individual. The synergistic effects associated with several other factors such as genetics, diet, and interactions with other toxins have been poorly studied. Therefore, it is possible that vitamin deficiency, caloric deprivation, alcohol abuse, and infectious disease status can all have compounded effects with mycotoxins.

Direct comparison of prior art mold-remediation technologies is difficult due to the differing modes of application and methods for measuring results. For example, fogging with chemical fungicides provides a one-time shock treatment of entire rooms or confined spaces, while ultraviolet (UV) light continuously treats the air stream in the air-handling system of a structure. While fogging a chemical fungicide will impact mold-spore source colonies, there is little or no residual effect to prevent re-infestation. UV irradiation, on the other hand, provides continuous eradication of mold spores in the air stream, but does nothing to eliminate the source colonies. UV installation is costly and does not eliminate mold that may enter a building through windows, doors, or any other avenue of ingress that is downstream of the UV generator and filter.

There is clearly a need for an improved mold cleaning product and a system for using that product to remedy mold infestation in residential and commercial properties.

SUMMARY OF THE INVENTION

A method of treating a building for mold contamination including the steps of assessing and locating mold growth areas, constructing a containment barrier around the mold growth areas, vacuuming, abrading and surface treating the mold growth areas, ceilings, walls and window treatments with mold cleaner, replacing air filters from air handlers, removing all registers and vent grills in the treated areas and washing the vent grills with mold cleaner, vacuuming all registers and accessible ductwork, treating the heating and ventilation system, associated ductwork and wall cavities with an atomized mold cleaner, vacuuming all flooring, horizontal surfaces, walls, furniture and mattresses, re-vacuuming all flooring, re-treating the heating and ventilation system and associated ductwork with an atomized mold cleaner and re-treating the work area including any exposed wall cavities with an atomized mold cleaner, deconstructing and discarding containment barrier and reinstalling all registers and vent grills.

DESCRIPTION OF THE DRAWINGS

FIG. 8 is a bar graph illustrating the data from Table 13.

DETAILED DESCRIPTION

Figure 1:
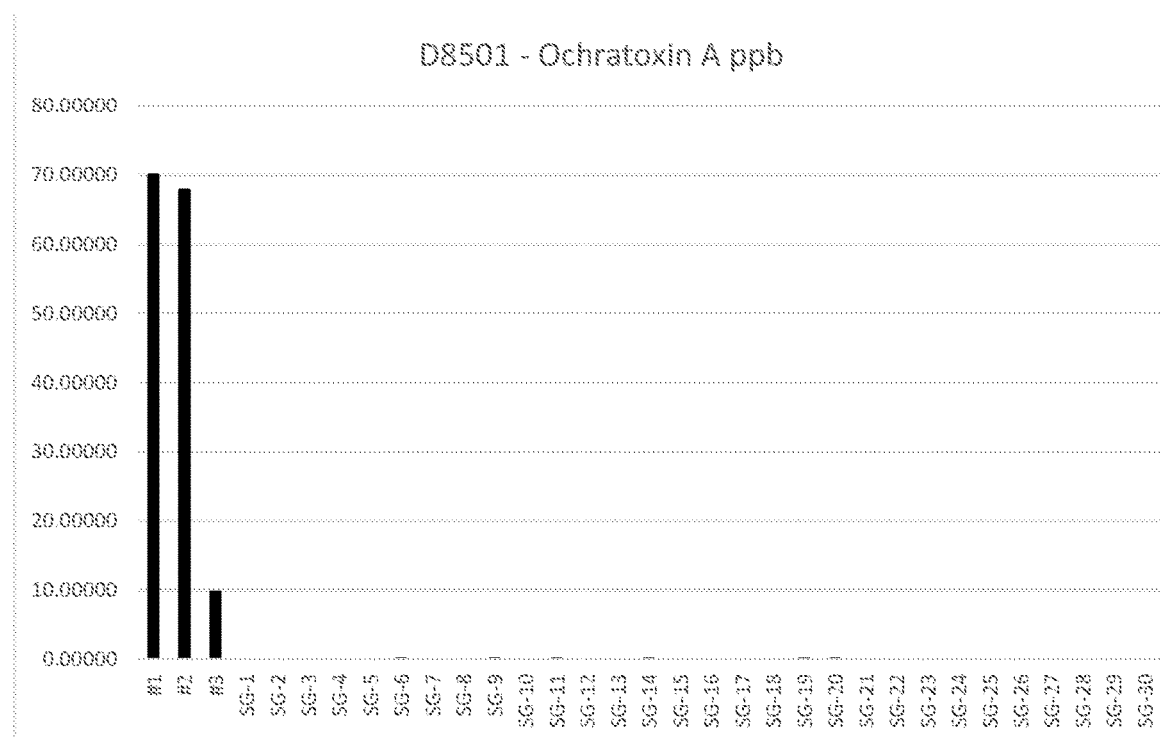
FIG. 1 is a bar graph illustrating the data from Table 6.

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

The instant invention includes a mold cleaning composition which is an enzymatic mold cleaner. The mold cleaning composition includes water, propylene glycol, one or more enzymes, one or more buffers, one or more surfactants, one or more biocides, one or more terpenes, one or more limonenes, or a combination thereof.

The water used in the instant invention is preferably selected from the group including distilled water, deionized water, filtered water, pharmaceutical grade water, and/or medical grade water.

Propylene glycol is an organic compound with the chemical formula $CH_3CH(OH)CH_2OH$. It is a viscous, colorless liquid, which is nearly odorless but possesses a faintly sweet taste. Containing two alcohol groups, it is classed as a diol. It is miscible with a broad range of solvents, including water, acetone, and chloroform. In general, glycols are non-irritating, have very low volatility and very low toxicity.

Enzymes are a substance that act as a catalyst in living organisms, regulating the rate at which chemical reactions proceed while avoiding alteration of itself during the process. Enzymes regulate most of the chemical reactions, and thus, the biological processes, that occur within living organisms. Enzymes catalyze all aspects of cell metabolism including the digestion of food, in which large nutrient molecules (i.e., proteins, carbohydrates, and fats) are broken down into smaller molecules. This same enzymatic activity can be used to treat and remove unwanted molds and other fungi. Examples of enzymes used in the instant invention include protease, lipase and amylase.

A buffer is a solution that can resist pH change upon the addition of acidic or basic components. It is able to neutralize small amounts of added acid or base, thus maintaining the pH of the solution as relatively stable. The buffering required to properly formulate the mold cleaner can be accomplished with any buffering agent known in the art (i.e., NaOH). One example of a buffer used in the instant invention is a phosphate ethanolamine buffer.

Surfactants are compounds that lower the surface tension (or interfacial tension) between two liquids, between a gas and a liquid, or between a liquid and a solid. Surfactants may act as detergents, wetting agents, emulsifiers, foaming agents, and dispersants. Examples of surfactants used in the instant invention include, but are not limited to, Polyglucose, cocamidopropyl betaine surfactant (Caltaine C-35 available from Pilot Chemical Company of Santa Fe Springs, CA, USA, and igepal—a nonionic, non-denaturing detergent (IGEPAL CA surfactants available from Rhodia of La Defense, France).

Biocidal products are intended to destroy, render harmless, prevent the action of, or otherwise exert a controlling effect on any harmful organism by chemical or biological means. Put another way, biocides are a diverse group of poisonous substances including preservatives, insecticides, disinfectants, and pesticides used for the control of organisms that are harmful to human or animal health or that cause damage to natural or manufactured products. One example of a biocide used in the instant invention is ESP Safeguard WS from Earth Supplied Products in Naples Florida Terpenes are a large and diverse class of organic compounds, produced by a variety of plants, particularly conifers, and by some insects. Examples of terpenes which can be included in the instant invention are limonene and D-lemonene. Limonene is a colorless liquid aliphatic hydrocarbon classified as a cyclic monoterpene and is the major component in the oil of citrus fruit peels. D-lemonene occurs in nature as the fragrance of oranges, is a flavoring agent in food manufacturing.

Tables 1 and 2 illustrate possible formulations for the mold cleaning composition used in the instant invention.

TABLE 1

| | Material | Component | Component % | | Total Formula % (w/w) | Mass (g) |
|---|---|---|---|---|---|---|
| 1 | Enzyme | Enzyme | 26.15% | 7.39% | 28.25% | 29.00 |
| | | Water | 73.85% | 20.86% | | |
| 2 | Propylene Glycol | | | 3.31% | 3.31% | 3.40 |
| 3 | Buffer | Salts | 13.30% | 3.08% | 23.13% | 23.75 |
| | | Water | 86.70% | 20.06% | | |
| 4 | Caltaine C-35 | surfactant | 30.00% | 0.58% | 1.95% | 2.00 |
| | | Water | 70.00% | 1.36% | | |
| 5 | Terpene | | | 0.12% | 0.12% | 0.12 |
| 6 | D-limonene | | | 1.11% | 1.11% | 1.14 |
| 7 | Igepal | surfactant | 70.00% | 0.51% | 0.73% | 0.75 |
| | | Water | 30.00% | 0.22% | | |
| 8 | ESP Safeguard WS XX | Biocide | 15.00% | 0.07% | 0.49% | 0.50 |
| | | Water | 85.00% | 0.41% | | |
| 9 | Water | | | 40.91% | 40.91% | 42.00 |
| | | | | Total Mass | | 102.66 |
| | | | | Water Content | | 83.19% |

TABLE 2

| | Material | Component | Component % | | Total Formula % (w/w) | Mass (g) |
|---|---|---|---|---|---|---|
| 1 | Enzyme | Enzyme | 26.15% | 7.53% | 28.81% | 29.00 |
| | | Water | 73.85% | 21.28% | | |
| 2 | Propylene Glycol | | | 3.38% | 3.38% | 3.40 |
| 3 | phosphate ethanolamine buffer | Salts | 13.30% | 3.14% | 23.60% | 23.75 |
| | | Water | 86.70% | 20.46% | | |
| 4 | polyglucose | surfactant | 30.00% | 0.60% | 1.99% | 2.00 |
| | | Water | 70.00% | 1.39% | | |
| 8 | ESP Safeguard WS XX | Biocide | 15.00% | 0.07% | 0.50% | 0.50 |
| | | Water | 85.00% | 0.42% | | |
| 9 | Water | | | 41.73% | 41.73% | 42.00 |
| | | | | Total Mass | | 100.65 |
| | | | | Water Content | | 84.86% |

The instant invention includes a method of treating a building for mold contamination comprising the steps of:
a. assessing and locating mold growth areas;
b. constructing a containment barrier around one or more areas to be treated to isolate designated areas from the rest of the structure, if necessary;
c. installing HEPA air scrubbers as needed;
d. vacuuming, abrading and surface treating exposed framing with visible microbial growth;
e. surface treating salvageable building materials with mold cleaner;
f. removing air filters from air handlers and disposing the filters;
g. removing all registers and vent grills in the treated areas;
h. washing the vent grills with mold cleaner;
i. vacuuming all registers and accessible ductwork;
j. vacuuming the interior of the air handler;
k. surface treating coils and sheet metal with mold cleaner;
l. treating the heating and ventilation system and associated ductwork with an atomized mold cleaner;
m. treating the work area including any exposed wall cavities with an atomized mold cleaner;
n. vacuuming all flooring;
o. surface treating the ceilings, walls and window treatments in affected areas with mold cleaner;
p. treating horizontal hard surfaces with mold cleaner;
q. vacuuming all horizontal hard surfaces;
r. vacuuming all walls;
s. vacuuming all upholstered furniture and mattresses;
t. vacuuming all flooring a second time;
u. treating the heating and ventilation system and associated ductwork with an atomized mold cleaner a second time;
v. treating the work area including any exposed wall cavities with an atomized mold cleaner a second time;
w. deconstructing the containment barrier;
x. discarding containment barrier; and
y. reinstalling all registers and vent grills.

In the above method:
the containment barrier can be constructed of a polysheeting material or similar material.
a vacuum equipped with an ultra low particulate air (ULPA) filter or similar filter with a minimum particle penetration size of 0.1 μm is used for all vacuuming to ensure the removal of 99.999% of mold, dust, pollen, bacteria and airborne particles.
the mold cleaner can be a surface enzymatic mold cleaner, an air/airborne enzymatic mold cleaner, or similar cleaner.
the atomized mold cleaner can be an air guard enzymatic mold cleaner or similar cleaner.
horizontal hard surfaces can include cabinets, counter tops, table-tops, dressers, nightstands, armoires, bookshelves and the like.
the air scrubbers can be high efficiency particulate air (HEPA) filter or similar filter which will remove at least 99.95% of particles whose diameter is equal to 0.3 μm from the air that passes through the filter.

Any method described herein may incorporate any design element contained within this application and any other document/application incorporated by reference herein.

EXAMPLES

Ochratoxin SOP: Clinical Determination of Ochratoxin
1. Purpose

The purpose of this document is to provide a procedure for the qualitative detection of Ochratoxin A in human tissue and human body fluids. The procedure is validated as a semiquantitative test and will be reported as "Present", "Not Present", or "Equivocal" values are reported as ng/dl (ppb). Values (in ppb) are determined and kept on the worksheets and placed in the worksheet manuals. Ochratoxin is produced by *Aspergillus ochraceus* and *Penicillium* species and has been reported in the medical literature to be associated with bladder infections, bladder and kidney tumors, and other urinary tract tumors. The test is a "home-brew" or Laboratory Determined Test (LDT) validation and has been validated at RTL in Dallas Texas using an ELISA plate with reagents to determine the levels of Ochratoxin A in human body fluids and tissues. This procedure is not intended for any other use but what has been validated at RTL. All ELISA tests are validated using Analyte Specific Reagents (ASRs) from Beacon Analytical Systems, Inc.

2. Principle of Procedure:

Competitive Direct Enzyme-Linked Immunosorbent Assay (ELISA)

The test is a competitive direct enzyme-linked immunosorbent assay (ELISA) which allows the user to obtain concentrations in parts per billion (ppb). Free Ochratoxin antigens in the patient samples and controls compete with enzyme-labeled Ochratoxin (conjugate) for the antibody binding sites inside the surface of the testing wells. After a wash step, substrate is added that reacts with the bound conjugate to produce a blue color. Addition of stop solution halts the reaction and changes the color to yellow.

Darker color=Lower concentration

Lighter color=Higher concentration

The test is read in a microplate reader to yield optical densities. The optical densities of the standards form a standard curve. Then, the sample optical densities are plotted against the curve to calculate the exact concentration of Ochratoxin A.

3. Safety:

Ochratoxins are highly toxic. All contaminated wells and trays should soak for 30 minutes in 10% bleach solution in a plastic container. After soaking in 10% bleach solution the trays should be washed off and the wells thrown away in the biohazard waste. Gloves and other protective apparel must be worn at all times. If liquid comes into contact with skin, wash immediately with soap and water.

4. Specimen:
   a. Urine is an acceptable specimen for this procedure. Urine specimens are collected in a supplied RTL plastic tube (plastic is preferred because of safety issues) and stored at 2-8° C. If specimen is to be held more than one week, specimens should be frozen in a designated freezer with a temperature range of −10 to −25° C. All urine specimens are to be diluted 1:7 in 10% MeOH/PBS for testing. After testing, all specimens are frozen and kept for a minimum of 6 months in a −10 to −25° C. freezer prior to disposal.
   b. Nasal and Mucus Secretions are acceptable specimens for this procedure. Nasal and mucus specimens are collected in supplied RTL kits and stored at 2-8° C. If specimen is to be held more than one week, specimens should be frozen at −10 to −25° C.
   c. Tissue Fixed in 10% Formalin is an acceptable specimen for this procedure. Tissue fixed in 10% Formalin specimens are collected in supplied RTL kits and stored at 2-8° C. Tissue fixed in a 10% formalin solution must be no more than 6 months old to prevent false negative results. Preparation of these samples is as follows:
      Weigh out 25-35 mg of formalin-fixed tissue and put into a blender. Pour enough PBS into the blender to cover blades (approximately 25 ml).
      Blend on high for 2 minutes (120 seconds). If mixture is still lumpy, blend tissue on high for 2 more minutes or until liquefied.
      Take a funnel and place a VICAM 24 cm fluted filter paper inside. Pour tissue mixture into the funnel and collect the liquid that drains through in a specimen tube. The sample may be tested immediately or stored at −10 to −25° C.
   d. Tissue Fixed in Paraffin Blocks is an acceptable specimen for this procedure. Tissue fixed in paraffin blocks are collected in supplied RTL kits. Blocks are cut by a commercial entity contracted by RTL. Fixed tissue in paraffin blocks containing autopsy or clinical biopsy tissue can be stored at room temperature. Preparation of these samples is as follows:
      Obtain 25-50 mg of tissue specimen off of the block (number of cuts and tubes to be determined by medical director).
      Add 0.3 g of silica beads.
      Add 1.5 mL of 10% Methanol/PBS.
      Bead beat for 1 minute.
      Place in heat block at 65° C. for 60 minutes.
      Bead beat for 1 minute.
      Centrifuge at 13,000 rpm for 2 minutes.
      Remove extract, taking care not to remove beads or paraffin, and place it into a specimen tube. Sample may be tested right away or stored at −10 to −25° C.

5. Materials:
   a. Reagents and Consumables:
      Ochratoxin—Beacon Kit—96 antibody-coated microwells (ELISA wells). (Store at 2-8° C., expiration per manufacturer) (Cat.No. 20-0294) (Beacon Analytical Systems, Inc., Saco, Maine)
      Ochratoxin—Beacon Kit 5 labeled bottles of 0, 0.5, 2, 5, and 10 ppb Ochratoxin calibrators. (Store at 2-8° C., expiration per manufacturer) (Cat.No. 20-0294) (Beacon Analytical Systems, Inc., Saco, Maine)
      Ochratoxin—Ochratoxin-A Enzyme Conjugate. (Store at −20° C., expiration per manufacturer) (Cat.No. 20-0294) (Beacon Analytical Systems, Inc., Saco, Maine
      Ochratoxin—HRP Ochratoxin A Diluent. (Store at 2-8° C., expiration per manufacturer) (Cat.No. 20-0294) (Beacon Analytical Systems, Inc., Saco, Maine)
      Ochratoxin—Beacon Kit 1 Substrate Solution (labeled brown bottle) (Store at 2-8° C., expiration per manufacturer) (Cat.No. 20-0294) (Beacon Analytical Systems, Inc., Saco, Maine)
      Ochratoxin—Beacon Kit 1 opaque white-labeled bottle of Stop Solution. (Store at 2-8° C., expiration per manufacturer) (Cat.No. 20-0294) (Beacon Analytical Systems, Inc., Saco, Maine)
      Ochratoxin High, Low and Negative Controls (Created in house from purchased stocks—see Creating Mycotoxin Standards and Control Procedure 20.4037) (Store at −10 to −25° C., expiration 6 months from date of preparation)
      10% MeOH/PBS
      Molecular grade water
      Acid-washed Silica beads Cat # G1277 (Obtained from Sigma-Aldrich) Note: Store all reagents as labeled when not in use. Do not expose reagents or plate to temperatures greater than 37° C. or less than 2° C. Allow all reagents to reach ambient temperature before use. Do not expose substrate to direct light prior to using the substrate in the test. Calculations for determinations are made knowing the exposure time of the substrate to the antigen/antibody mixture.
   b. Equipment:
      Positive displacement pipettes to deliver 6.0 mL, 100.0 μL, and 1,000.0 μL
      Pipette tips (10.0 mL, 200.0 μL and 1,000.0 μL)
      1 empty plate tray for well strips (marked in sharpie)
      Microplate Spectrophotometer/Computer with Softmax Pro software and internet/UniFlow access
      Distilled or deionized water
      Squirt Bottle to fill with DI H$_2$O
      Squirt Bottle to fill with Beacon wash solution
      Timer
      Orbital plate shaker
      Tube vortex
      Tube rack Reagent reservoir holder and disposable reservoirs
10.0 mL tubes for sample dilutions
Bottle of prepared 10% MeOH/PBS
Plastic container with prepared 10% Bleach
Plastic container with prepared 70% EtOH
Paper towels 6. Quality Control:
   a. Validation and Proficiency Testing: Samples processed according to this procedure have been validated for the semiquantitative determination of Ochratoxin. Proficiency testing of this mycotoxin will be processed according to the proficiency testing SOP and the proficiency testing schedule.
   b. Assay Calibrators: Five Ochratoxin calibrators are provided with the kit and processed along with the patient samples. The calibrators are provided at 0, 0.5, 2, 5, and 10 ppb and during analysis, a semi-log curve fit for the standard curve is used to plot the points of the calibrators. A correlation coefficient of >95% is acceptable.
   c. Assay Controls: Three Ochratoxin controls are created by RTL and processed along with the patient samples and calibrators. These three controls include a high Ochratoxin control, a low Ochratoxin control, and a negative Ochratoxin control. To determine if these controls are acceptable and in range, they are compared to the current control ranges which are provided to the lab and recalculated and updated with each lot of control. For run acceptance, two of the three controls must be within the current control ranges, and the negative control must not be "Equivocal" or "Present."
   d. Calculations embedded in UniFlow are used to perform analysis of Ochratoxin testing. The formulas embedded in these worksheets were validated as equivalent to those provided by the manufacturer for this product and are checked during the course of proficiency testing by utilizing the known proficiency test samples.

7. Reagent Lots:
   Reagent Lot to Lot Testing: New plate lots are tested in parallel with the plate lot currently in use. To test the new lot, three samples (two positive and one negative) are processed using the same protocol for both the new lot and the old lot. All kit lot numbers and lot test results are recorded in the Reagent Lot Log and in UniFLow under QC Resources>Reagents. After the test is completed, the new lot of reagents is qualified in UniFLow>QC Resources>Qualify Reagent as "Passed" and are ready for use.

8. Procedure:
   a. Worksheet Generation:
      1. Review pending samples using the sample database and generate a worksheet for the mycotoxin testing to be run.
      2. Initial, Date, and Record Lot Numbers on this worksheet. Note: This information will be transferred on to the UniFlow electronic worksheet during the data analysis steps.
   b. Sample Preparation:
      1. Controls are made in a negative urine sample (<2.0 ppb Ochratoxin). Control lot numbers are entered into the Reagent section in UniFlow.
      2. All urine samples are to be diluted 1:7 in a 10% MeOH/PBS solution to remove the matrix effect of the urine.
   c. Setup and Run:
      1. Pull out all needed reagents and samples for the run. Allow both the reagents and samples to come to room temperature. (Thawing of the samples may be required)
      2. Organize samples according to the run worksheet in a sample tube rack. Place a 10.0 mL tube with each sample for sample dilution.
      3. Once all components have reached room temperature, remove the antibody coated wells from the container pouch. Take out 5 of the antibody coated wells and place them in column 1 vertically on an empty plate tray labeled OA (Ochratoxin A) for the standards. Take 3 antibody wells and put them in column 2 vertically on the plate tray for each of the controls. Take out as many wells as samples in the run and put them vertically in columns 4, 5, 6 . . . etc. Return unneeded strips to pouch and reseal. Put the tray with wells for the run in a plastic bag with a desiccant, squeeze out as much air as possible, and seal (wells are sensitive to humidity and this will protect the wells until you are ready to proceed with the run).
      4. Add 6.0 mL of 10% MeOH/PBS to the 10.0 mL dilution tubes for each sample. Individually double check each sample with the run worksheet, invert and vortex the sample tube a couple times to mix, then pipette 1,000.0 µL into the 10.0 mL tubes with MeOH/PBS (this creates the 1:7 dilution of the samples). After the sample dilutions are complete vortex each of the 10 mL dilution tubes. Note: If running the Ochratoxin A procedure along with the Tricothecene or Gliotoxin, the sample is already diluted 1:5 in the 10.0 mL tubes in front of each sample. If this is the case, only add 2.0 mL of 10% MeOH/PBS to achieve a dilution ratio of samples to 1:7. After adding the additional 2.0 mL, vortex each of the tubes.
      5. Next, take out the tray with wells from plastic bag and add 100.0 µl of calibrators, controls, and samples to Ochratoxin A antibody-coated wells. The calibrators and samples are added in ascending fashion, and the controls are added as high, low, and negative in ascending order. All controls are made from the Ochratoxin A stock bottle kept in the freezer at or near −10 to −25 degrees Celsius. This solution is stored in 10% MeOH/PBS Buffer.
      6. After pipetting into the wells, place tray on shaker at 80-100 rpm, set timer for 20 minutes, start the timer, and allow tray to incubate.
      7. After incubation add 100.0 µL of Ochratoxin-A Enzyme Conjugate to all wells.
      8. After pipetting into the wells, place tray on orbital shaker at 80-100 rpm, set timer for 20 minutes, start the timer, and allow tray to incubate at room temperature.
      9. Once time is up, empty liquid from the tray into the sink and wash the wells 4 times with Beacon Wash Solution from the squirt bottle (prepared by adding one packet to 1 L DI H2O).
      10. Lay clean paper towels on the counter, flip tray over, and tap tray over paper towels to remove left over $H_2O$ in the wells. Wipe any residual water on the outside of the wells with the paper towel.
      11. Take tray back to bench and add 100.0 µl of substrate to all the wells.

12. Put tray back on shaker and set the timer for 10 minutes. Incubate at room temperature.
13. Finally, add 100.0 μl of stop solution, put back on shaker for 5 minutes, and then read plate. Proceed to Spectrophotometric Measurement in procedure below. Note: Read the plate within 30 minutes of the addition of Stop Solution.
14. After plate is read, put whole tray with wells into 10% bleach in plastic container. Submerge and let soak for 30 minutes to decontaminate. After 30 minutes, dump wells into biohazard waste and rinse tray with water in sink. Set tray on clean paper towel to air dry. Once dry, put tray away for later use on another run.
15. Once the run is complete and accepted all samples should be stored in a designated freezer. All reagents need to be put back into the refrigerator at 2-8° C. as soon as possible. Decontaminate the bench work surfaces and pipettes with 10% bleach spray, followed with 70% Methanol.

d. Spectrophotometric Measurement:
1. Turn on SpectraMax 190. Turn on computer and monitor. Login.
2. Start program SoftMax Pro 4.8. Adjust settings by choosing Control>Instrument Setup. Set wavelength to 450 nm for measurement. Check box for Pre-Read.
3. Once plate is ready to read, insert empty "blank" plate. Click Read. Software will ask to confirm Pre-Read. Click OK. Drawer will close and blank instrument.
4. Remove empty plate and insert test plate. Click Read. Software will ask to confirm Read. Click OK. Drawer will close and read test plate.
5. To save read, click File>Save as. Name by date, test, worksheet number, technician initials, and instrument ID (e.g. 110813ochra.1013.atm.A) and save to appropriate folder. Print results, date and initial.
6. To save as .txt format for upload to UniFlow, click File>Export. Save under same file name as .pdf format.
7. To shut down instrument, close drawer using software or Drawer button on instrument. Power switch is located on right rear. Cover with dust cover. Close program and shut down computer.

e. Data Analysis:
1. Open Ochratoxin worksheet in UniFlow using the laboratory computer.
2. Enter the lot numbers for reagents and controls. Click Submit. This will move the worksheet to the Upload Ochra Results step.
3. Click Upload Ochra Results. Choose the worksheet from the dropdown menu. Click Choose File and locate the correct file for the worksheet. Click Submit. This will move the worksheet into the Review Ochra Results step.

f. Results Interpretation:
1. Review the results by opening Review Ochra Results and selecting the worksheet from the dropdown menu. Print the Results.
2. Assay Calibrators: Five Ochratoxin calibrators are provided with the kit and processed along with the patient samples. The calibrators are provided at 0, 0.5, 2, 5, and 10 ppb and during analysis, a semi-log curve fit for the standard curve is used to plot the points of the calibrators. A correlation coefficient of >95% is acceptable.
3. Assay Controls: Three Ochratoxin controls are created by RTL and processed along with the patient samples and calibrators. These three controls include a high Ochratoxin control, a low Ochratoxin control, and a negative Ochratoxin control. To determine if these controls are acceptable and in range, they are compared to the current control ranges which are provided to the lab and recalculated and updated with each lot of control. For run acceptance, two of the three controls must be within the current control ranges and the negative control must not be "Equivocal" or "Present."
4. If the above calibrators and controls are approved then results will be determined to be "Present", "Not Present", or "Equivocal" based on the standard curve analysis. Limit of Detection (LOD) in this test has been determined to be 2.0 ppb. Thus, any values less than 1.8 ppb will be reported as "Not Present". Values of 2.0 or greater will be reported as "Present". Values of 1.8-2 will be reported as "Equivocal". Ppb results will be maintained in the lab on worksheets, in the UniFlow LIS system, and listed on the reports.

Aflatoxin SOP: Clinical Determination of Aflatoxin

1. Purpose

The purpose of this document is to provide a procedure for the qualitative detection of Aflatoxin B1, B2, G1, G2, and others such as P1 and M in human tissue and human body fluids. The procedure is validated as a semiquantitative test and will be reported out "Positive", "Negative", or "Equivocal" Values are also reported as ppb (ng/dL). Values (in ppb) are determined and kept on the worksheets and placed in the worksheet manuals. Aflatoxins are produced by *Aspergillus* and have been reported in the medical literature to be associated with lung, liver, and other malignancies. The test is a Laboratory Determined Test (LDT) and has been validated at RTL in Dallas Texas using an ELISA plate with reagents to determine the levels of Aflatoxin in human body fluids and tissues. This procedure is not intended for any other use but what has been validated at RTL. All ELISA tests are validated using Analyte Specific Reagents (ASRs) from Beacon Analytical Systems Inc.

2. Principle of Procedure:

Competitive Direct Enzyme-Linked Immunosorbent Assay (ELISA)

The test is a competitive direct enzyme-linked immunosorbent assay (ELISA) which allows the user to obtain concentrations in parts per billion (ppb). Free aflatoxin antigens in the patient samples, calibrators, and controls compete with enzyme-labeled aflatoxin (conjugate) for the antibody binding sites inside the surface of the testing wells. After a wash step, substrate is added that reacts with the bound conjugate to produce a blue color. Addition of stop solution halts the reaction and changes the color to yellow.

Darker color=Lower concentration

Lighter color=Higher concentration

The test is read in a microwell reader to yield optical densities. The optical densities of the calibrators form the standard curve. Then, the sample optical densities are plotted against the curve to calculate the exact concentration of Aflatoxin.

3. Safety:

Aflatoxins are highly toxic. All contaminated wells and trays should soak for 30 minutes in 10% bleach solution in a plastic container. After soaking in 10% bleach solution the trays should be washed off and the wells discarded in the biohazard waste. Gloves and other protective apparel must be worn at all times. If liquid comes into contact with skin, wash immediately with soap and water.

4. Specimen:
   a. Urine is an acceptable specimen for this procedure. Urine specimens are collected in a supplied RTL plastic tube (plastic is preferred because of safety issues) and stored at 2-8° C. If specimen is to be held more than one week, specimens should be frozen at −10 to −25° C. All urine specimens are to be diluted 1:7 in 10% MeOH/PBS for testing. After testing, all specimens are frozen and kept for a minimum of 7 days in a −10 to −25° C. freezer prior to disposal.
   b. Nasal and Mucus Secretions are acceptable specimens for this procedure. Nasal and mucus specimens are collected in supplied RTL kits and stored at 2-6° C. If specimen is to be held more than one week, specimens should be frozen at −10 to −25° C.
   c. Tissue Fixed in 10% Formalin is an acceptable specimen for this procedure. Tissue fixed in 10% Formalin specimens are collected in supplied RTL kits and stored at 2-8° C. Tissue fixed in a 10% formalin solution must be no more than 6 months old to prevent false negative results. Preparation of these samples is as follows:
      Weigh out 25-35 mg of formalin-fixed tissue and put into a blender. Pour enough PBS into the blender to cover blades (approximately 25 ml).
      Blend on high for 2 minutes (120 seconds). If mixture is still lumpy, blend tissue on high for 2 more minutes or until liquefied.
      Take a funnel and place a VICAM 24 cm fluted filter paper inside. Pour tissue mixture into the funnel and collect the liquid that drains through in a specimen tube. The sample may be tested immediately or stored at −10 to −25° C.
   d. Tissue Fixed in Paraffin Blocks is an acceptable specimen for this procedure. Tissue fixed in paraffin blocks are collected in supplied RTL kits. Blocks are cut by a commercial entity contracted by RTL. Fixed tissue in paraffin blocks containing autopsy or clinical biopsy tissue can be stored at room temperature. Preparation of these samples is as follows:
      Obtain 25-50 mg of tissue specimen off of the block (number of cuts and tubes to be determined by medical director).
      Add 0.3 g of silica beads.
      Add 1.5 mL of 10% Methanol/PBS.
      Bead beat for 1 minute.
      Place in heat block at 65° C. for 60 minutes.
      Bead beat for 1 minute.
      Centrifuge at 13,000 rpm for 2 minutes.
      Remove extract, taking care not to remove beads or paraffin, and place it into a specimen tube. Sample may be tested right away or stored at −10 to −25° C.

5. Materials:
   a. Reagents and Consumables:
      Aflatoxin High Sensitivity Kit: (Cat.No20-0290) (Beacon Analytical Systems Inc. Saco, Maine)
         96 antibody coated wells per package plate, store at 2-8° C.
         96 red marked mixing wells per plate, store at 2-8° C.
         Conjugate, store at 2-8° C.
         Substrate, store at 2-8° C.
         Stop solution, store at 2-8° C.
         Wash packet, store at 2-8° C. Dissolve in 1 L DI water for use.
      Aflatoxin High, Low and Negative Controls; store at 2-8° C. when in use. (Store at −10 to −25° C. prior to use, expiration 6 months from date of preparation)
      Aflatoxin calibrators of 0, 1, 2, 4, 8 ppb; store at store at 2-8° C. when in use. (Store at −10 to −25° C. prior to use., expiration 6 months from date of preparation)
      10% MeOH/PBS
      Molecular grade water
      Acid-washed Silica beads Cat # G1277 (Obtained from Sigma-Aldrich).
      Note: Store all reagents at 2-8° C. when not in use. Do not expose reagents or plate to temperatures greater than 37° C. or less than 2° C. Allow all reagents to reach ambient temperature before use. Do not expose substrate to direct light prior to using the substrate in the test. Calculations for determinations are made knowing the exposure time of the substrate to the antigen/antibody mixture.
   b. Equipment:
      Positive displacement pipettes to deliver 6.0 mL, 100.0 μL, and 1,000.0 μL
      Pipette tips (10.0 mL, 200.0 μL and 1,000.0 μL)
      2 empty plate trays for well strips (marked to identify for aflatoxin use).
      Microplate Spectrophotometer/Computer with Softmax Pro software and internet/UNIFlow access
      Distilled or deionized water
      Squirt Bottle to fill with DI $H_2O$
      Squirt Bottle to fill with Beacon wash solution
      Timer
      Orbital plate shaker
      Tube vortex
      Tube rack
      Reagent reservoir holder and disposable reservoirs
      10.0 mL tubes for sample dilutions
      Bottle of prepared 10% MeOH/PBS
      Plastic container with prepared 10% Bleach
      Plastic container with prepared 70% EtOH
      Paper towels 6. Quality Control:
   a. Validation and Proficiency Testing: Samples processed according to this procedure have been validated for the semiquantitative determination of Aflatoxin. (See Process Validation Protocol-Aflatoxin) Proficiency testing of this mycotoxin will be processed according to the proficiency testing SOP and the proficiency testing schedule.
   b. Assay Calibrators: Five aflatoxin calibrators are created by RTL and processed along with the patient samples. The calibrators are at 0, 1, 2, 4, and 8 ppb. During analysis a semi-log curve fit for the standard curve is used to plot the points of the calibrators. A correlation coefficient of >95% is acceptable.
   c. Assay Controls: Three aflatoxin controls are created by RTL and processed along with the patient samples and calibrators. These three controls include a high aflatoxin control, a low aflatoxin control and a negative aflatoxin control. To determine if these controls are acceptable and in range they are compared to the current control ranges which are provided to the lab and recalculated and updated with each lot of control. For run acceptance two of the three controls must be within the current control ranges, and the negative control must not be "Equivocal" or "Positive."
   d. Calculations embedded in UNIFlow are used to perform analysis of Aflatoxin testing. The formulas embedded in these worksheets were validated as equivalent to those provided by the manufacturer for this product and are checked during the course of proficiency testing by utilizing the known proficiency test samples.

7. Reagent Lots:

Reagent Lot to Lot Testing: New plate lots are tested in parallel with the plate lot currently in use. In order to test the new lot, three samples (two positive and one negative) are processed using the same protocol for both the new lot and the old lot. An alternative method would be to test a known positive from the previous lot and compare the results of the new lot to the old lot. All kit lot numbers and lot test results are recorded in the Reagent Lot Log and in UNIFlow under QC Resources>Reagents. After the test is completed, the new lot of reagents is Qualified in UNIFlow>QC Resources>Qualify Reagent as "Passed" and is ready for use.

8. Procedure:

a. Worksheet Generation:
      1. Review pending samples using the sample database and generate a worksheet for the mycotoxin testing to be run. (See SOP LAB.2031)
      2. Initial, Date, and Record Lot Numbers on this worksheet. Note: This information will be transferred on to the UNIFlow electronic worksheet during the data analysis steps.

b. Sample/Control/Solution Preparation:
      1. Aflatoxin calibrators are prepared and held in 10% MeOH/PBS Buffer. Calibrators are as follows: Negative (PBS+MeOH-10%); 0.0 ppb, 1.0 ppb, 2.0 ppb, 4.0 ppb, and 8.0 ppb. Calibrators are labeled with preparation date and expiration date and initialed by preparer. Calibrators and Controls are to be created and stored in amber bottles. At the expiration date, the amber bottles are opened and soaked in a 10% bleach solution for one hour prior to discarding the bottles in a hazardous waste container.
      2. Controls are made in a negative urine sample (<1.0 ppb Aflatoxin). Control lot numbers are entered into the Reagent section in UNIFlow.
      3. All urine samples are to be diluted 1:7 in a 10% MeOH/PBS solution to remove the matrix effect of the urine.

c. Setup and Run:
      1. Pull out all needed reagents and samples for the run. Allow both the reagents and samples to come to room temperature. (Thawing of the samples may be required)
      2. Organize samples according to the run worksheet in a sample tube rack. Place a 10.0 mL tube with each sample for sample dilution.
      3. Remove the antibody coated wells, with one of the two plates for marked for aflatoxin use add wells as follows. Take out 5 of the antibody coated wells and place them in column 1 vertically (wells A1-E1) for each of the calibrators. Take out 3 wells and place them in column 2 vertically (wells A2-C2) for each of the controls. Take out as many wells as samples in the run and put them vertically in columns 4, 5, 6 . . . etc. Return unneeded strips to pouch and reseal. Remove red mixing wells from the container pouch, with the second marked aflatoxin tray add mixing wells as previously described. Put the trays with wells for the run in a plastic bag with desiccant, squeeze out as much air as possible, and seal (wells are sensitive to humidity and this will protect the wells until you are ready to proceed with the run).
      4. Add 6.0 mL of 10% MeOH/PBS to the 10.0 mL dilution tubes for each sample. Individually double check each sample with the run worksheet, invert the sample tube a couple times to mix, then pipette 1,000.0 μL into the 10.0 mL tubes with MeOH/PBS (this creates the 1:7 dilution of the samples). After the sample dilutions are complete vortex each of the 10 mL dilution tubes. Note: If running the Aflatoxin procedure along with the Tricothecene, Tricothecenes are usually started first so the sample is already diluted 1:5 in the 10.0 mL tubes for each sample. If this is the case, only add 2.0 mL of 10% MeOH/PBS in order to get dilution of samples to 1:7. After adding the additional 2.0 mL, vortex each of the tubes.
      5. Next, take out tray with wells from plastic bag and add 100.0 μl of conjugate to all the red mixing wells in the tray. Then, add 100.0 μl of calibrators, controls, and samples to the appropriate red mixing wells. The calibrators and samples are added in ascending fashion, and the controls are added as high, low, and negative in order. All controls are made from the aflatoxin stock bottle kept in the freezer at or near −10 to −25 degrees Celsius at a concentration of 200 ppm. This solution is stored in MeOH. Return calibrators and controls to refrigerator immediately after use.
      6. Mix the contents of the red mixing wells by pipetting up and down 3 times. Then take 100.0 μl of the mixture and transfer to the corresponding antibody coated wells on the plate tray.
      7. After pipetting into the wells, place tray on orbital shaker at 80-100 rpm, set timer for 15 minutes, start the timer, and allow tray to incubate at room temperature.

Ensure light source has been turned off as the substrate is very sensitive to light and may cause low readings.
      8. Once time is up, empty liquid from the tray into the sink and wash the wells 4 times with Beacon Wash Solution from the squirt bottle.
      9. Set a clean paper towel on the counter, flip tray over, and tap tray over paper towel to remove left over Wash Solution in the wells. Wipe any residual water on the outside of the wells with the paper towel.
      10. Take tray back to bench and add 100.0 μl of substrate to all the wells.
      11. Put tray back on shaker and set the timer for 10 minutes. Incubate at room temperature.
      12. Finally, add 100.0 μl of stop solution, put back on shaker for 5 minutes, and then read plate. Proceed to Spectrophotometric Measurement in procedure below. Note: Read the plate within 30 minutes of the addition of Stop Solution.
      13. After plate is read, put whole tray with wells into 10% bleach in plastic container. Submerge and let soak for 30 minutes to decontaminate. After 30 minutes, dump wells into biohazard waste and rinse tray with water in sink. Set tray on clean paper towel to air dry. Once dry, put tray away for later use on another run.
      14. Once the run is complete and accepted, all samples should be stored in a designated freezer. All reagents need to be put back into the refrigerator at 2-8° C. as soon as possible. Decontaminate the bench work surfaces and pipettes with 10% bleach, followed by 70% Methanol.

d. Spectrophotometric Measurement:
1. Turn on SpectraMax 190. Turn on computer and monitor. Login. Start program SoftMax Pro 4.8. Adjust settings by choosing Control>Instrument Setup. Set wavelength to 450 nm for measurement. Check box for Pre-Read.
2. Once plate is ready to read, insert empty "blank" plate. Click Read. Software will ask to confirm Pre-Read. Click OK. Drawer will close and blank instrument.
3. Remove empty plate and insert test plate. Click Read. Software will ask to confirm Read. Click OK. Drawer will close and read test plate.
4. To save read, click File>Save as. Name by date, test, worksheet number, and technician initials (e.g. 110813afla.1011.atm) and save to appropriate folder. Print results, date and initial.
5. To save as .txt format for upload to UNIFlow, click File>Export. Save under same file name as .pdf format.
6. To shut down instrument, close drawer using software or Drawer button on instrument. Power switch is located on right rear. Close program and shut down computer.

e. Data Analysis:
1. Open Aflatoxin Worksheet in UNIFlow using the laboratory computer.
2. Enter the lot numbers for reagents and controls. Click Submit. This will move the worksheet to the Upload Afla Results step.
3. Click Upload Afla Results. Choose the worksheet from the dropdown menu. Click Choose File and locate the correct file for the worksheet. Click Submit. This will move the worksheet into the Review Afla Results step.
4. The UNIFlow statistics software plots the calibrators entered into a semi-log curve to generate a standard curve. Controls and samples are plotted on a graph to give results in parts per billion (ppb) or nanograms/ml f. Results Interpretation:
1. Review the results by opening Review Afla Results and selecting the worksheet from the dropdown menu. Print the Results.
2. Assay Calibrators: Five aflatoxin calibrators are created by RTL and processed along with the patient samples. The calibrators are provided at 0, 1, 2, 4, and 8 ppb and during analysis a semi-log curve fit for the standard curve is used to plot the points of the calibrators. A correlation coefficient of >95% is acceptable.
3. Assay Controls: Three aflatoxin controls are created by RTL and processed along with the patient samples and calibrators. These three controls include a high aflatoxin control, a low aflatoxin control and a negative aflatoxin control. To determine if these controls are acceptable and in range they are compared to the current control ranges which are provided to the lab and recalculated and updated with each lot of control. For run acceptance two of the three controls must be within the current control ranges, and the negative control must not be "Equivocal" or "Positive." Controls are plotted and reviewed monthly using Levey-Jennings charts.
4. If the above calibrators and controls are approved then results will be determined to be "Positive" or "Negative", or "Equivocal" based on the standard curve analysis. Limit of Detection in this test has been determined to be 1.0 ppb. Thus, any values less than 0.8 ppb will be reported as "Negative". Values of 1.0 or greater will be reported as "Positive". Values of 0.8-1.0 will be reported as "Equivocal". Ppb results will be maintained in the lab on worksheets, in the UNIFlow LIS system, and listed on the reports.

Trichothecene (Macrocyclic) SOP: Clinical Determination of Trichothecene

1. Purpose:
The purpose of this document is to provide a procedure for the qualitative detection of Tricothecenes including Roridin A, E, H, and L-2, Satratoxin G and H, Isosatratoxin F, Verrucarin A and J, and Verrucarol in human tissue and human body fluids. The procedure is validated as a semi-quantitative test and will be reported out as "Present", "Not Present", or "Equivocal". Values are also reported as ng/dL (ppb). Values (in ppb) are determined and kept on the worksheets and placed in the worksheet manuals. The test is a "home-brew" or Laboratory Determined Test (LDT) that has been validated at RTL in Dallas, Texas The test consists of using an ELISA plate and Analyte Specific Reagents (ASRs) obtained from Beacon Analytical Systems, Inc. to determine the levels of Tricothecene in human body fluids and tissues. This procedure is not intended for any other use but what has been validated at RTL.

2. Principle of Procedure:
Competitive Direct Enzyme-Linked Immunosorbent Assay (ELISA)
The test is a competitive direct enzyme-linked immunosorbent assay (ELISA) which allows the user to obtain concentrations in parts per billion (ppb) when results are compared to a standard curve. Free Trichothecene antigens in the patient samples and controls compete with enzyme-labeled Trichothecene (conjugate) for the antibody binding sites inside the surface of the testing wells. After a wash step, substrate is added that reacts with the bound conjugate to produce a blue color. Addition of stop solution halts the reaction and changes the color to yellow.
Darker color=Lower concentration
Lighter color=Higher concentration
The test is read in a microtiter plate reader and data is expressed as to yield optical densities. The optical densities of the controls form the standard curve. Then, the sample optical densities are plotted against the curve to calculate the exact concentration of Trichothecene.

3. Safety:
Trichothecenes are highly toxic. All contaminated wells and trays should soak for 30 minutes in 10% bleach solution in a plastic container. After soaking in 10% bleach solution the trays should be washed off and the wells thrown away in the biohazard waste. Gloves and other protective apparel must be worn at all times. If liquid comes into contact with skin, wash immediately with soap and water.

4. Specimen:
a. Urine is an acceptable specimen for this procedure. Urine specimens are collected in a RTL supplied plastic tube (plastic is preferred because of safety issues) and stored in a designated refrigerator with a temperature range of 2-8° C. If specimen is to be held more than one week, specimens should be frozen in a designated freezer with a temperature range of −10 to −25° C. All urine specimens are to be diluted 1:5 in 10% MeOH/

PBS for testing. After testing, all specimens are frozen and kept for a minimum of 7 days in a −10 to −25° C. freezer prior to disposal.
  b. Nasal and Mucus Secretions are acceptable specimens for this procedure. Nasal and mucus specimens are collected in supplied RTL kits and stored in a designated refrigerator with a temperature range of 2–8° C. If specimen is to be held more than one week, specimens should be frozen in a designated freezer with a temperature range of −10 to −25° C.
  c. Tissue Fixed in 10% Formalin is an acceptable specimen for this procedure. Specimens fixed in 10% Formalin are collected in supplied RTL kits and stored in a designated refrigerator with a temperature range of 2–8° C. Tissue fixed in a 10% formalin solution must be no more than 6 months old to prevent false negative results. Preparation of these samples is as follows:
    Weigh out 25-35 mg of formalin-fixed tissue and put into a blender. Pour enough PBS into the blender to cover blades (approximately 25 ml).
    Blend on high for 2 minutes (120 seconds). If mixture is still lumpy, blend tissue on high for 2 more minutes or until liquefied.
    Take a funnel and place a VICAM 24 cm fluted filter paper inside. Pour tissue mixture into the funnel and collect the liquid that drains through in a specimen tube. The sample may be tested immediately or stored in a designated freezer with a temperature range of −10 to −25° C.
  d. Tissue Fixed in Paraffin Blocks is an acceptable specimen for this procedure. Tissue fixed in paraffin blocks are collected in supplied RTL kits. Blocks are cut by a commercial entity contracted by RTL. Fixed tissue in paraffin blocks containing autopsy or clinical biopsy tissue can be stored at room temperature. Preparation of these samples is as follows:
    Obtain 25-50 mg of tissue specimen off of the block (number of cuts and tubes to be determined by medical director).
    Add 0.3 g of silica beads.
    Add 1.5 mL of 10% Methanol/PBS.
    Bead beat for 1 minute.
    Place in heat block at 65° C. for 60 minutes.
    Bead beat for 1 minute.
    Centrifuge at 13,000 rpm for 2 minutes.
    Remove extract, taking care not to remove beads or paraffin, and place it into a specimen tube. Sample may be tested right away or stored at −10 to −25° C.
5. Materials:
  a. Reagents and Consumables:
    Trichothecene—96 Roridin A antibody-coated microwells (ELISA wells) in plate frame. (Store at 2-8° C., expiration per manufacturer) (Cat.No. 20-0175) (Beacon Analytical Systems, Inc., Saco, Maine)
    Trichothecene—Roridin A Enzyme Conjugate. (Store at 2-8° C., expiration per manufacturer) (Cat.No. 20-0175) (Beacon Analytical Systems, Inc., Saco, Maine)
    Trichothecene—HRP Roridin A Diluent. (Store at 2-8° C., expiration per manufacturer) (Cat.No. 20-0175) (Beacon Analytical Systems, Inc., Saco, Maine)
    Trichothecene—Substrate. (Store at 2-8° C., expiration per manufacturer) (Cat.No. 20-0175) (Beacon Analytical Systems, Inc., Saco, Maine)
    Trichothecene—Stop Solution. (Store at 2-8° C., expiration per manufacturer) (Cat.No. 20-0175) (Beacon Analytical Systems, Inc., Saco, Maine)
    Trichothecene 0.0, 0.01, 0.03, 0.1, 0.3, and 1.0 ppb calibrators (Store at −10 to −25.9° C., expiration 6 months from date of preparation) (Cat. No. 20-0175) (Beacon Analytical Systems, Inc., Saco, Maine)
    Trichothecene High, Low and Negative Controls (Created in house from purchased stocks—see Creating Mycotoxin Standards and Control Procedure 20.4037) (Store at −10 to −25.9° C., expiration 6 months from date of preparation)
    10% MeOH/PBS
    Water, Deionized, NCCLS Type 1 (CLRVV)
    Acid-washed Silica beads Cat # G1277 (Obtained from Sigma-Aldrich).
    Note: Store all reagents at 2-8° C. when not in use. Do not expose reagents or plate to temperatures greater than 37° C. or less than 2° C. Allow all reagents to reach ambient temperature before use. Do not expose substrate to direct light prior to using the substrate in the test. Calculations for determinations are made knowing the exposure time of the substrate to the antigen/antibody mixture.
  b. Equipment:
    Positive displacement pipettes to deliver 4.0 mL, 20 uL, 100.0 μL, and 1,000.0 μL
    Pipette tips (10.0 mL, 20 μL, 200.0 μL and 1,000.0 μL)
    Empty plate trays for well strips
    Microplate Spectrophotometer/Computer with SoftMax Pro software and Internet/UniFlow Access
    Distilled or deionized water
    Squirt Bottle to fill with DI $H_2O$
    Timer
    Orbital plate shaker
    Tube vortex
    Tube rack
    Reagent reservoir holder and disposable reservoirs
    10.0 mL tubes for sample dilutions
    Bottle of prepared 10% MeOH/PBS
    Plastic container with prepared 10% Bleach
    Plastic container with prepared 70% EtOH
    Paper towels
    15 ml conical tube
6. Quality Control:
  a. Validation and Proficiency Testing: Samples processed according to this procedure have been validated for the semiquantitative determination of Trichothecene. (See Process Validation Protocol-Trichothecene) Proficiency testing of this mycotoxin will be processed according to the proficiency testing SOP and the proficiency testing schedule.
  b. Assay Calibrators: Six Trichothecene calibrators are created by RTL and processed along with the patient samples. The calibrators are at 0.0, 0.01, 0.03, 0.1, 0.3, and 1.0 ppb and during analysis a semi-log curve fit for the standard curve is used to plot the points of the calibrators. A correlation coefficient of >95% is acceptable.
  c. Assay Controls: Three Trichothecene controls are created by RTL and processed along with the patient samples and calibrators. These three controls include a high Trichothecene control, a low Trichothecene control, and a negative Trichothecene control. To determine if these controls are acceptable and in range, they are compared to the current control ranges which are provided to the lab and recalculated and updated with each lot of control. For run acceptance, two of the three controls must be within the current control ranges, and the negative control must not be "Equivocal" or "Positive.".

d. Calculations embedded in UniFlow (Laboratory Information System) are used to perform analysis of Tricothecene testing. The formulas embedded in these worksheets were validated as equivalent to those provided by the manufacturer and are checked during the course of proficiency testing by utilizing the known proficiency test samples.

7. Reagent Lots:

Reagent Lot to Lot Testing: New plate lots are tested in parallel with the plate lot currently in use. In order to test the new lot, three samples (two positive and one negative) are processed using the same protocol for both the new lot and the old lot. All kit lot numbers and lot test results are recorded in the Reagent Lot Log and in UniFLow under QC Resources>Reagents. After the test is completed, the new lot of reagents is Qualified in UniFLow>QC Resources>Qualify Reagent as "Passed" and is ready for use. Record all lot numbers and lot test results in the Reagent Lot Log (10.7G). Further reference is made to the Lot to Lot comparison Standard Operating Procedure.

8. Procedure:

a. Worksheet Generation:
1. Review pending samples using the sample database and generate a worksheet for the mycotoxin testing to be run.
2. Initial, Date, and Record Lot Numbers on this worksheet. Note: This information will be entered into the UniFlow electronic worksheet during the data analysis steps.

b. Sample/Control/Solution Preparation:
1. Trichothecene calibrators are prepared and held in 10% MeOH/PBS Buffer. Calibrators are as follows: Negative (PBS+MeOH −10%); 0.01, 0.03, 0.1, 0.3, and 1.0 ppb. Calibrators are labeled with date and expiration date and initialed by preparer. Calibrators and Controls are to be created and stored in amber bottles. At the expiration date, the amber bottles are opened and soaked in a 10% bleach solution for one hour prior to discarding the bottles in a hazardous waste container.
2. Controls are made in a negative urine sample (<0.2 ppb Trichothecene). (See SOP LAB.4061) Control lot numbers are entered into the Reagent section in UniFlow.
3. All urine samples are to be diluted 1:5 in a 10% MeOH/PBS solution to remove the matrix effect of the urine.
4. Prepare conjugate by Diluting Roridin A HRP stock 1:1500 into HRP diluent. Typical preparation of conjugate batch requires 7 µL of HRP stock to 10.5 mL of HRP diluent in a 15 ml conical tube. Label the tube with a new lot number (HRP lot#—date, e.g. 1050E-022014). Store at 2-8° C.

c. Setup and Run:
1. Pull out all needed reagents and samples for the run. Allow both the reagents and samples to come to room temperature. (Thawing of the samples is required).
2. Organize samples according to the run worksheet in a sample tube rack. Place a 10.0 mL tube with each sample for sample dilution.
3. Remove the Roridin A antigen coated plate from the container pouch. Take out 4 wells and place them in column 1 vertically for each of the calibrators. Take out 3 wells and put them in column 2 vertically for each of the controls. Take out as many wells as samples in the run and put them vertically in columns 4, 5, 6 . . . etc. Return unneeded strips to pouch and reseal. Place a desiccant in the bag with the tray.
4. Add 4.0 mL of 10% MeOH/PBS to the 10.0 mL dilution tubes for each sample. Individually double check each sample with the run worksheet, vortex the sample tube several times to mix, then pipette 1,000.0 µL into the 10.0 mL tubes with MeOH/PBS (this creates the 1:5 dilution of the samples). After all samples in the run are diluted, vortex each of the 10.0 mL dilution tubes.
5. Next, take out the tray with wells from plastic bag and add 100.0 µl of calibrators, controls, and samples to appropriate wells. The standards and samples are added in ascending fashion, and the controls are added as high, low, and negative in order. All calibrators are made from the Verrucarin A Control bottle kept in the freezer at or near −10 to −25.9 degrees Celsius at a concentration of 200 ppm. This solution is stored in 10% MeOH/PBS Buffer. Return all standards and controls to the refrigerator as soon as possible.
6 After pipetting into the wells, place tray on orbital shaker at 80-100 rpm, set timer for 15 minutes, start the timer, and allow tray to incubate at room temperature.
7. After incubation add 100.0 µL of conjugate to all wells.
8. Place tray on the shaker, set timer for 15 minutes and incubate at room temperature.
9. After incubation, empty liquid from the tray into the sink and wash all wells 4 times with DI $H_2O$ from the squirt bottle.
10. Set a clean paper towel on the counter, flip tray over, and tap tray over paper towel to remove left over $H_2O$ in the wells. Wipe any residual water on the outside of the wells with the paper towel.
11. Take tray back to bench and add 100.0 µl of substrate to all the wells.
12. Put tray back on shaker and set the timer for 30 minutes. Incubate at room temperature and away from direct light.
13. Finally, add 100.0 µl of stop solution, put back on shaker for 5 minutes, and then read plate. Proceed to Spectrophotometric Measurement in the procedure below. Note: Read the plate within 30 minutes of the addition of Stop Solution.
14. After plate is read, put whole tray with wells into 10% bleach in plastic container. Submerge and let soak for 30 minutes to decontaminate. After 30 minutes, dump wells into biohazard waste and rinse tray with water in sink. Set tray on clean paper towel to air dry. Once dry, put tray away for later use on another run.
15. Once the run is complete and accepted all samples should be stored in a designated freezer. All reagents need to be put back into the refrigerator at 2-8° C. as soon as possible, and decontamination of the bench work surfaces and pipettes need to be done with 10% bleach, followed by 70% Methanol.

d. Spectrophotometric Measurement:
1. Turn on SpectraMax 190. Turn on computer and monitor. Ctl+Alt+Del to Login with User: Name and password.

2. Start program SoftMax Pro 4.8. Adjust settings by choosing Control>Instrument Setup. Set wavelength to 450 nm for measurement. Check box for Pre-Read.
3. Once plate is ready to read, insert empty "blank" plate. Click Read. Software will ask to confirm Pre-Read. Click OK. Drawer will close and blank instrument.
4. Remove empty plate and insert test plate. Click Read. Software will ask to confirm Read. Click OK. Drawer will close and read test plate.
5. To save read, click File>Save as. Name by date, test, worksheet number, technician initials and instrument ID: "a" or "b" depending the Spectrometer used. (e.g. 110813tricho.1010.atm.a) and save to appropriate folder. Print results, date and initial.
6. To save as .txt format for upload to UniFlow, click File>Export. Save under same file name as .pdf format.
7. To shut down instrument, close drawer using software or Drawer button on instrument. Power switch is located on right rear. Cover with dust cover. Close program and shut down computer.

e. Data Analysis:
1. Open Trichothecene Worksheet in UniFlow using the laboratory computer.
2. Enter the lot numbers for reagents and controls. Click Submit. This will move the worksheet to the Upload Tricho Results step.
3. Click Upload Tricho Results. Choose the worksheet from the dropdown menu. Click Choose File and locate the correct file for the worksheet. Click Submit. This will move the worksheet into the Review Tricho Results step.
4. The UniFlow statistics software plots the calibrators entered into a semi-log curve to generate a standard curve. Controls and samples are plotted on a graph to give results in parts per billion (ppb) or nanograms/ml. (See example of the data reduction worksheet, graph.

f. Results Interpretation:
1. Review the results by opening Review Tricho Results and selecting the worksheet from the dropdown menu. Print the Results.
2. Assay Calibrators: Four Trichothecene calibrators are created by RTL and processed along with the patient samples. The calibrators are at 0, 0.01, 0.03, 0.1, 0.3, and 1.0 ppb and during analysis, a semi-log curve fit for the standard curve is used to plot the points of the calibrators. A correlation coefficient of >95% is acceptable.
3. Assay Controls: Three Trichothecene controls are created by RTL and processed along with the patient samples and calibrators. These three controls include a high Trichothecene control, a low Trichothecene control and a negative Trichothecene control. To determine if these controls are acceptable and in range they are compared to the current control ranges which are provided to the lab and recalculated and updated with each lot of control. For run acceptance two of the three controls must be within the current control ranges, and the negative control must not be "Equivocal" or "Positive." Controls are plotted and reviewed monthly using Levey-Jennings charts.
4. If the above calibrators and controls are approved then results will be determined to be "Positive" or "Negative", or "Equivocal" based on the standard curve analysis. Limit of Detection in this test has been determined to be <0.02 ppb. Thus, any values less than 0.02 ppb will be reported as "Negative". Values of 0.03 ppb or greater will be reported as "Positive". Values of 0.02<0.03 ppb will be reported as "Equivocal". Ppb results will be maintained in the lab on worksheets, in the UniFlow LIS system, and listed on the reports.

Gliotoxin Derivative SOP: Clinical Determination of Bis (methylthio)gliotoxin

1. Purpose:
The purpose of this document is to provide a procedure for the qualitative detection of Gliotoxin in human tissue and human body fluids. The procedure is validated as a semi-quantitative test and will be reported out "Present", "Not Present", or "Equivocal" Values are also reported as ng/dl (ppb). Values (in ppb) are determined and kept on the worksheets and placed in the worksheet manuals. Gliotoxin is a sulfur-containing mycotoxin produced by several species of fungi, including pathogens of humans such as *Aspergillus fumigatus* and also by species of *Trichoderma*, and *Penicillium*. Gliotoxin possesses immunosuppressive properties as it may suppress and cause apoptosis in certain types of cells of the immune system. The test is a Laboratory Determined Test (LDT) and has been validated at RTL in Carrollton, Texas using an ELISA plate with reagents to determine the levels of Gliotoxin in human body fluids and tissues. The test uses bis(methylthio)gliotoxin (SS-dimethyl-gliotoxin (bmGT)) as diagnostic marker of pathologies caused by gliotoxin-producing fungi or their derivatives. bmGT is a metabolite and an analog of gliotoxin (GT) shown to be a more sensitive marker than GT in the diagnosis of aspergillosis. Results have shown that bmGT can be detected in biological samples of immunodepressed patients with a high reliability, sensitivity and specificity[1]. This procedure is not intended for any other use but what has been validated at RTL. All ELISA tests are validated using Analyte Specific Reagents (ASRs) from Beacon Analytical systems Inc.

2. Principle of Procedure:
Competitive Direct Enzyme-Linked Immunosorbent Assay (ELISA)
The test is a competitive direct enzyme-linked immunosorbent assay (ELISA), which allows the user to obtain concentrations in parts per billion (ppb). Gliotoxin antigens in the patient samples and controls compete with enzyme-labeled bmGT-HRP (conjugate) for the antibody binding sites inside the surface of the testing wells. After a wash step, substrate is added that reacts with the bound conjugate to produce a blue color. Addition of stop solution halts the reaction and changes the color to yellow.
  Darker color=Lower concentration
  Lighter color=Higher concentration
The test is read in a microwell reader to yield optical densities. The optical densities of the controls form the standard curve. Then, the sample optical densities are plotted against the curve to calculate the exact concentration of bis(methylthio)gliotoxin.

3. Safety:
Gliotoxins are toxic. All contaminated wells and trays should soak for 30 minutes in 10% bleach solution in a plastic container. After soaking in 10% bleach solution the trays should be washed off and the wells thrown away in the biohazard waste. Gloves and other protective apparel must be worn at all times. If liquid comes into contact with skin, wash immediately with soap and water.

4. Specimen:
   a. Urine is an acceptable specimen for this procedure. Urine specimens are collected in a supplied RTL plastic tube (plastic is preferred because of safety issues) and stored at 2-8° C. If specimen is to be held more than one week, specimens should be frozen at −10 to −25° C. All urine specimens are to be diluted 1:5 in 10% MeOH/PBS for testing. After testing, all specimens are frozen in a −10 to −25° C. freezer and kept for a minimum of 6 months prior to disposal.
5. Materials:
   a. Reagents and Consumables:
      bmGT Test using the Bis MethylthioGliotoxin (bmGT) 96 antibody-coated microwells (ELISA wells. Store at 2-8° C., expiration per manufacturer (Beacon Analytical Systems Inc, Saco, Maine)
      Bis MethylthioGliotoxin (bmGT) ELISA Kit—96 antibody-coated microwells (ELISA wells). Store at 2-8° C., expiration per manufacturer (Beacon Analytical Systems Inc, Saco, Maine)
      Bis MethylthioGliotoxin (bmGT) ELISA Kit with 5 amber bottles of 0, 0.3, 1, 3, and 10 ppb calibrators. Store at 2-8° C., expiration per manufacturer (Beacon Analytical Systems Inc, Saco, Maine)
      Bis MethylthioGliotoxin (bmGT) ELISA Kit-HRP conjugate solution diluent. Store at 2-8° C., expiration per manufacturer (Beacon Analytical Systems Inc, Saco, Maine)
      Bis MethylthioGliotoxin (bmGT) ELISA Kit—HRP dried conjugate. Reconstituted with 5 mLs HRP diluent provided prior to use. Store at −10 to −25° C., expiration per manufacturer (Beacon Analytical Systems Inc, Saco, Maine)
      Bis MethylthioGliotoxin (bmGT) ELISA Kit Substrate Solution (amber bottles) Store at 2-8° C., (Beacon Analytical Systems Inc, Saco, Maine)
      Bis MethylthioGliotoxin (bmGT) ELISA Kit-clear Stop Solution (white bottle) Store at 2-8° C., (Beacon Analytical Systems Inc, Saco, Maine)
      Bis MethylthioGliotoxin (bmGT) ELISA Kit Wash solution. Store at 2-8° C., expiration per manufacturer. For use, dissolve contents of the packet in 1 L distilled water. Store at 20-25° C. Discard solution after one week. (Beacon Analytical Systems Inc, Saco, Maine)
      bmGT High, Low and Negative Controls (Created in house from purchased stocks) (Store at −10 to −25° C., expiration 6 months from date of preparation);
      10% MeOH/PBS (Various Vendors); Molecular grade water.
   b. Equipment:
      Pipette tips (10.0 mL, 200.0 μL and 1,000.0 μL)
      2 empty plate trays for well strips (marked in sharpie for Gliotoxin testing)
      Microplate Spectrophotometer/Computer with Softmax Pro software
      Distilled or deionized water
      Squirt Bottle to fill with DI $H_2O$
      Squirt Bottle to fill with Beacon wash solution
      Timer
      Plate shaker
      Tube vortex
      Tube rack
      Reagent reservoir holder and disposable reservoirs
      10.0 mL tubes for sample dilutions
      Bottle of prepared 10% MeOH/PBS
      Plastic container with prepared 10% Bleach
      Paper towels
6. Quality Control:
   a. Validation and Proficiency Testing: Samples processed according to this procedure have been validated for the semiquantitative determination of bmGT. (See Process Validation Protocol—bmGT) Proficiency testing of this mycotoxin will be processed according to the proficiency testing SOP and the proficiency-testing schedule.
   b. Assay Calibrators: Five bmGT calibrators are provided with the kit and processed along with the patient samples. The calibrators are provided at 0, 0.3, 1, 3, and 10 ppb and during analysis a semi-log curve fit for the standard curve is used to plot the points of the calibrators. A correlation coefficient of >95% is acceptable.
   c. Assay Controls: Three bmGT controls are created by RTL and processed along with the patient samples and calibrators. These three controls include a high bmGT control, a low bmGT control and a negative bmGT control. To determine if these controls are acceptable and in range they are compared to the current control ranges, which are provided to the lab and recalculated and updated with each lot of control. For run acceptance two of the three controls must be within the current control ranges, and the negative control must be below the cutoff value.
   d. Calculations embedded in UNIFlow are used to perform analysis of Gliotoxin testing. The formulas embedded in these worksheets were validated as equivalent to those provided by the manufacturer for this product and are checked during the course of proficiency testing by utilizing the known proficiency test samples.
7. Reagent Lots:
   Reagent Lot to Lot Testing: New plate lots are tested in parallel with the plate lot currently in use. In order to test the new lot, three samples (two positive and one negative) are processed using the same protocol for both the new lot and the old lot. An alternative method would be to test a known positive from the previous lot and compare the results of the new lot to the old lot. All kit lot numbers and lot test results are recorded in the Reagent Lot Log and in UNIFlow under QC Resources>Reagents. After the test is completed, the new lot of reagents is placed in the gliotoxin container and can be ready for use.
8. Procedure:
   a. Worksheet Generation:
      1. Review pending samples using the sample database and generate a worksheet for the mycotoxin testing to be run. (See SOP 10.2031)
      2. Initial, Date, and Record Lot Numbers on this worksheet. Note: This information will be transferred on to the UNIFlow electronic worksheet during the data analysis steps.
   b. Sample Preparation:
      1. Controls are made in a negative urine sample (<0.25 ppb gliotoxin). (See Creating Mycotoxin Standards and Control Procedure 20.4037) Control lot numbers are entered into the Reagent section in UNIFlow.
      2. All urine samples are to be diluted 1:5 in a 10% MeOH/PBS solution to remove the matrix effect of the urine. (See setup and Run below)

c. Setup and Run:
   1. Pull out and prepare all needed reagents and samples for the run. Allow both the reagents and samples to come to room temperature. (Thawing of the samples may be required). Add 5 mLs of HRP diluent to the bottle of died HRP conjugate, vortex for 30 seconds, and allow to sit for 30 minutes prior to use.
   2. Organize samples according to the run worksheet in a sample tube rack. Place a 10.0 mL tube with each sample for sample dilution.
   3. Once all components have reached room temperature, remove the bmGT antibody coated plate from the container pouch. Take out 5 wells and place them vertically in wells A1-E1 for each of the calibrators. Take out 3 wells and put them vertically in wells A2-C2 for each of the controls. Take out as many wells as samples in the run and put them vertically in columns 4, 5, 6 . . . etc. Return unneeded strips to pouch and reseal. Put the tray with wells for the run in a plastic bag, squeeze out as much air as possible, and seal (wells are sensitive to humidity and this will protect the wells until you are ready to proceed with the run).
   4. Add 4.0 mL of 10% MeOH/PBS to the 10.0 mL tubes in front of each sample. Individually double check each sample with the run worksheet, invert the sample tube a couple times to mix, then pipette 1,000.0 µL into the 10.0 mL tubes with MeOH/PBS (this creates the 1:5 dilution of the samples). After all samples in the run are diluted, gently vortex each of the 10.0 mL dilution tubes.
   5. Next, take out the tray with wells from plastic bag and add 100.0 µl of calibrators (standards), controls, and samples to bmGT antibody-coated wells. The standards and samples are added in ascending fashion, and the controls are added as high, low, and negative in order . . . . All controls are made from the bmGT Control bottle kept in the freezer at −10 to −25.9 degrees Celsius at a concentration of 200 ppm. This solution is stored in 10% MeOH/PBS Buffer.
   6. After pipetting into the wells, place tray on shaker at 80-100 rpm, set timer for 30 minutes, start the timer, and allow tray to incubate.
   7. After incubation add 100.0 µL of the previously reconstituted HRP conjugate to all wells.
   8. After pipetting into the wells, place tray on shaker at 80-100 rpm, set timer for 30 minutes, start the timer, and allow tray to incubate. Once time is up, take tray over to sink and wash the wells 4 times with Beacon Wash Solution from the squirt bottle (prepared by adding one packet to 1 L DI H2O).
   9. Set a clean paper towel on the counter, flip tray over, and tap tray over paper towel to remove residual solution in the wells. Wipe any residual solution on the outside of the wells with the paper towel.
   10. Take tray back to bench and add 100.0 µl of substrate to all the wells.
   11. Put tray back on shaker and set the timer for 30 minutes. Incubate.
   12. Finally, add 100.0 µl of stop solution, put back on shaker for 5 minutes, and then read plate. Proceed to Spectrophotometric Measurement in procedure below. Note: Read the plate within 30 minutes of the addition of Stop Solution.
   13. After plate is read, put whole tray with wells into 10% bleach in plastic container. Submerge and let soak for 30 minutes to decontaminate. After 30 minutes, dump wells into biohazard waste and rinse tray with water in sink. Set tray on clean paper towel to air dry. Once dry, put tray away for later use on another run.
   14. Once the run is complete and accepted all samples should be stored in a designated freezer. All reagents need to be put back into the refrigerator at 2-8° C. as soon as possible. Decontaminate the bench work surfaces and pipettes with 10% bleach spray, followed with 70% Methanol.
d. Spectrophotometric Measurement:
   1. Turn on SpectraMax 190. Turn on computer and monitor. Login.
   2. Start program SoftMax Pro 4.8. Adjust settings by choosing Control>Instrument Setup. Set wavelength to 450 nm for measurement. Check box for Pre-Read.
   3. Once plate is ready to read, insert empty "blank" plate. Click Read. Software will ask to confirm Pre-Read. Click OK. Drawer will close and blank instrument.
   4. Remove empty plate and insert test plate. Click Read. Software will ask to confirm Read. Click OK. Drawer will close and read test plate.
   5. To save read, click File>Save as Name by date, test, worksheet number, technician initials, and instrument ID (e.g. 110813glio.1011.atm.A) and save to appropriate folder. Print results, date and initial.
   6. To save as .txt format for upload to UNIFIow, click File>Export. Save under same file name as .pdf format.
   7. To shut down instrument, close drawer using software or Drawer button on instrument. Power switch is located on right rear. Close program and shut down computer.
e. Data Analysis:
   1. Open the Gliotoxin Worksheet in UniFLow using the laboratory computer.
   2. Enter the lot numbers for reagents and controls. Click Submit. This will move the worksheet to the Upload Glio Results step.
   3. Click Upload Glio Results. Choose the worksheet from the dropdown menu. Click Choose File and locate the correct file for the worksheet. Click Submit. This will move the worksheet into the Review Glio Results step.
   4. The UNIFIow statistics software plots the calibrators entered into a semi-log curve to generate a standard curve. Controls and samples are plotted on a graph to give results in parts per billion (ppb) or nanograms/ml.
f. Results Interpretation:
   1. Review the results by opening Review Glio Results and selecting the worksheet from the dropdown menu. Print the Results.
   2. Assay Calibrators: Five bmGT calibrators are provided with the kit and processed along with the patient samples. The calibrators are provided at 0, 0.3, 1, 3, and 10 ppb and during analysis a semi-log curve fit for the standard curve is used to plot the points of the calibrators. A correlation coefficient of >95% is acceptable.
   3. Assay Controls: Three bmGT controls are created by RTL and processed along with the patient samples and calibrators. These three controls include a high bmGT control, a low bmGT control, and a bmGT control. To determine if these controls are acceptable and in range, they are compared to the current control ranges which are provided to the lab and recalculated and updated with each lot of control. For run acceptance, two of the three controls must be within the current control ranges, and the negative control must not be "Equivocal" or "Positive." Controls are plotted monthly using Levey-Jennings charts.
4. If the above calibrators and controls are approved, then results will be determined to be "Positive" or "Negative", or "Equivocal" based on the standard curve analysis. Limit of Detection (LOD) in this test has been determined to be <0.5 ppb. Thus, any values less than 0.5 ppb will be reported as "Negative". Values of 1.0 or greater will be reported as "Positive". Values of 0.5-1.0 ppb will be reported as "Equivocal". Ppb results will be maintained in the lab on worksheets, in the UniFlow LIS system, and listed on the reports.
5. If the processed sample results, before the factoring dilution, are greater than the highest calibration sample (10.0 ppb), the numeric result is not to be reported. Instead, the sample will be reported as "greater than AMR (Analytical Measurement Range)".

Testing Analysis:

Three separate environmental mycotoxin and *Candida auris* tests accepted by a laboratory from three separate clients on environmental homes were conducted. All specimens had 15 mycotoxins and the fungus *Candida auris* was added to the specimen(s) prior to any extraction or processing of the 3 environmental specimens.

General Studies Description:

The aim of the study was to test the hypothesis that the fungi cleaning composition (FCC) could eliminate the presence of mycotoxins and *Candida auris* from an environmental specimen taken from a building such as a home or office. The project was a one (1) year study which began on Nov. 16, 2018 and ended by testing the last specimen on or about Nov. 21, 2019. The specimens were tested quarterly for one year using the Enzyme Labeled Immuno Sorbant-Assay (ELISA).

Methods: (Mycotoxins and *Candida auris*):

1. Sample Preparation and Storage during testing:

All specimens were handled in the same way throughout the study. Sterile gauze was inoculated with 100 μl of extracted environmental solution and placed in a sterile biohazard bag. The bags were separated into 6 separate groups and then placed in a clean polystyrene container. Samples were removed and dated with identification numbers 1-30. Only samples from the polystyrene container were tested.

2. Inoculation of solutions:

Specimens were taken from previous positive environmental solutions which were previous environmental home samples with requests for testing positive for 15 mycotoxins by ELISA testing. The test solutions also contained an inoculum of *Candida auris* which was placed in the solutions and tested. Controls in ELISA and PCR testing for *Candida auris* consisted of:

sterile gauze, phosphate buffered saline (extraction fluid), and

FCC or No FCC.

To ensure that the mycotoxins were remaining in the original specimens prior to treatment, a mycotoxin test was conducted on all three environmental home specimens at the end of the study.

Dates of testing: Specimens were tested prior to gauze inoculation. The samples were labeled in the following way: Date of inoculation, Date of Testing, Sample Number, and technologist initials preparing samples. Testing Standard Operating Procedures (SOPs) are as follows:

Samples 1-5; note samples were tested two hours after inoculation.

| | | |
|---|---|---|
| Date of Testing: | (1 Day) | Samples # 1-5 |
| | (30 days) | Samples # 6-10 |
| | (90 days) | Samples # 11-15 |
| | (180 days) | Samples # 16-20 |
| | (270 days). | Samples # 21-25 |
| | (365 days). | Samples # 26-30 |
| | (391 days). | Previous known positive samples. |

*Candida auris* testing. Two samples from each environmental home test were tested for a total of 6 tests.

Inoculation of samples: Approximately 0.5 ml of a 200 CFUs (colony forming units) per ml was conducted giving a final CFU count of 100 CFUs in each sample.

Testing: All six samples were tested for the presence of *C. auris* by Polymerase Chain Reaction (PCR).

Results:

Mycotoxin Testing (1 Year Total)

Results demonstrated that 15 mycotoxins were present in the environmental samples taken prior to any exposure to mold cleaner. Mycotoxin testing performed at the dates described above, provided the following mycotoxins (See Table1 below). Summary of results are shown below. A more thorough explanation of interpretation of mycotoxin results and PCR results with their respective graphs and charts are provided in the Exhibits of the study.

*Candida auris* Results:

PCR results for *Candida auris* for specimens were:

Specimens #1, #2, and #3 which had no mold cleaner sprayed on gauze:

all Positive at Day 0.

Specimens #4, #5, and #6 which had mold cleaner sprayed on Gauze at 100 ppb:

all Negative at Day 365.

All controls showed no *Candida auris*.

TABLE 3

| List of Mycotoxins tested in the Panel: | |
|---|---|
| D8501 - | Ochratoxin A |
| D8502 - | Aflatoxin Group B (B1, B2, G1, G2) |
| D8503 - | Trichothecene Group (Macrocyclic): Roridin A, Roridin E, Roridin H, Roridin L-2, Verrucarin A, Verrucarin J, Satratoxin G, Satratoxin H, Isosatratoxin F |
| D8510 - | Gliotoxin Derivative |

RESULTS:

| | Not present if less than: | Present if greater than: |
|---|---|---|
| D8501 - | 1.80000 ppb | 2.00000 ppb |
| D8502 - | 0.80000 ppb | 1.00000 ppb |
| D8503 - | 0.02000 ppb | 0.03000 ppb |
| D8510 - | 0.50000 ppb | 1.00000 ppb |

TABLE 4

Five Samples tested on six dates:

|  | Nov. 16, 2018 | Dec. 16, 2018 | Feb. 16, 2019 | May 16, 2019 | Aug. 16, 2019 | Nov. 21, 2019 |
|---|---|---|---|---|---|---|
| Sample One | SG-1 | SG-6 | SG-11 | SG-16 | SG-21 | SG-26 |
| Sample Two | SG-2 | SG-7 | SG-12 | SG-17 | SG-22 | SG-27 |
| Sample Three | SG-3 | SG-8 | SG-13 | SG-18 | SG-23 | SG-28 |
| Sample Four | SG-4 | SG-9 | SG-14 | SG-19 | SG-24 | SG-29 |
| Sample Five | SG-5 | SG-10 | SG-15 | SG-20 | SG-25 | SG-30 |

| Date of Testing: DAY ZERO | Starting Value (ppb): | | | |
|---|---|---|---|---|
| Test solutions PRIOR to treatment with MOLD CLEANER | D8501 | D8502 | D8503 | D8510 |
| SAMPLE #1 | >70 | 2.03000 | 0.59500 | 7.43500 |
| SAMPLE #2 | 67.68500 | 2.14300 | 0.36900 | 5.02500 |
| SAMPLE #3 | 9.75500 | 299.10000 | 0.16100 | 2.69700 |

TABLE 5

Results of Mycotoxin testing on three separate environmental samples prior to treatment with mold cleaner.

| Mycotoxins | #1 | #2 | #3 |
|---|---|---|---|
| Ochratoxin | >70 ppb* | 67.685 ppb | 9.755 ppb |
| Aflatoxins | 2.03 ppb | 2.143 pbb | 299.1 ppb |
| Trichothecenes | 0.595 ppb | 0.369 ppb | 0.161 ppb |
| Gliotoxin derivative | 7.435 ppb | 5.025. pbb | 2.697 ppb |

*ppb = parts per billion

Mycotoxin Results of all samples and all days 1-365 days which were treated with FCC were 0.00 ppb.

All controls showed no mycotoxins.

The original home environmental specimens were tested after one year. Although there was some decrease in quantity of mycotoxins, there was no complete eradication of the mycotoxins when compared to the results of the mold cleaner timing study.

Data:

TABLE 6

D8501 - Ochratoxin A

| Test Date | Sample | ppb |
|---|---|---|
| Day 0 | #1 | 70.00000 |
| Day 0 | #2 | 67.85000 |
| Day 0 | #3 | 9.75500 |
| Day 1 | SG-1 | 0.03000 |
| Day 1 | SG-2 | 0.02500 |
| Day 1 | SG-3 | 0.00500 |
| Day 1 | SG-4 | 0.02600 |
| Day 1 | SG-5 | 0.00500 |
| Day 30 | SG-6 | 0.05800 |
| Day 30 | SG-7 | 0.02000 |
| Day 30 | SG-8 | 0.02300 |
| Day 30 | SG-9 | 0.09400 |
| Day 30 | SG-10 | 0.05300 |
| Day 90 | SG-11 | 0.06000 |
| Day 90 | SG-12 | 0.03900 |
| Day 90 | SG-13 | 0.04000 |
| Day 90 | SG-14 | 0.07600 |
| Day 90 | SG-15 | 0.03500 |
| Day 180 | SG-16 | 0.04900 |
| Day 180 | SG-17 | 0.04300 |
| Day 180 | SG-18 | 0.04700 |
| Day 180 | SG-19 | 0.12600 |
| Day 180 | SG-20 | 0.07200 |
| Day 270 | SG-21 | 0.00800 |
| Day 270 | SG-22 | 0.02900 |
| Day 270 | SG-23 | 0.02900 |
| Day 270 | SG-24 | 0.02100 |
| Day 270 | SG-25 | 0.02200 |
| Day 365 | SG-26 | 0.04000 |
| Day 365 | SG-27 | 0.02600 |
| Day 365 | SG-28 | 0.01000 |
| Day 365 | SG-29 | 0.02300 |
| Day 365 | SG-30 | 0.01600 |

See also FIG. 1 graph for illustration.

TABLE 7

D8501 - Ochratoxin A

| Test Date | Sample | ppb |
|---|---|---|
| Day 1 | SG-1 | 0.03000 |
| Day 1 | SG-2 | 0.02500 |
| Day 1 | SG-3 | 0.00500 |
| Day 1 | SG-4 | 0.02600 |
| Day 1 | SG-5 | 0.00500 |
| Day 30 | SG-6 | 0.05800 |
| Day 30 | SG-7 | 0.02000 |
| Day 30 | SG-8 | 0.02300 |
| Day 30 | SG-9 | 0.09400 |
| Day 30 | SG-10 | 0.05300 |
| Day 90 | SG-11 | 0.06000 |
| Day 90 | SG-12 | 0.03900 |
| Day 90 | SG-13 | 0.04000 |
| Day 90 | SG-14 | 0.07600 |
| Day 90 | SG-15 | 0.03500 |
| Day 180 | SG-16 | 0.04900 |
| Day 180 | SG-17 | 0.04300 |
| Day 180 | SG-18 | 0.04700 |
| Day 180 | SG-19 | 0.12600 |
| Day 180 | SG-20 | 0.07200 |
| Day 270 | SG-21 | 0.00800 |
| Day 270 | SG-22 | 0.02900 |
| Day 270 | SG-23 | 0.02900 |
| Day 270 | SG-24 | 0.02100 |
| Day 270 | SG-25 | 0.02200 |
| Day 365 | SG-26 | 0.04000 |
| Day 365 | SG-27 | 0.02600 |
| Day 365 | SG-28 | 0.01000 |
| Day 365 | SG-29 | 0.02300 |
| Day 365 | SG-30 | 0.01600 |
| Defined | Present | 2.00000 |

Figure 2:
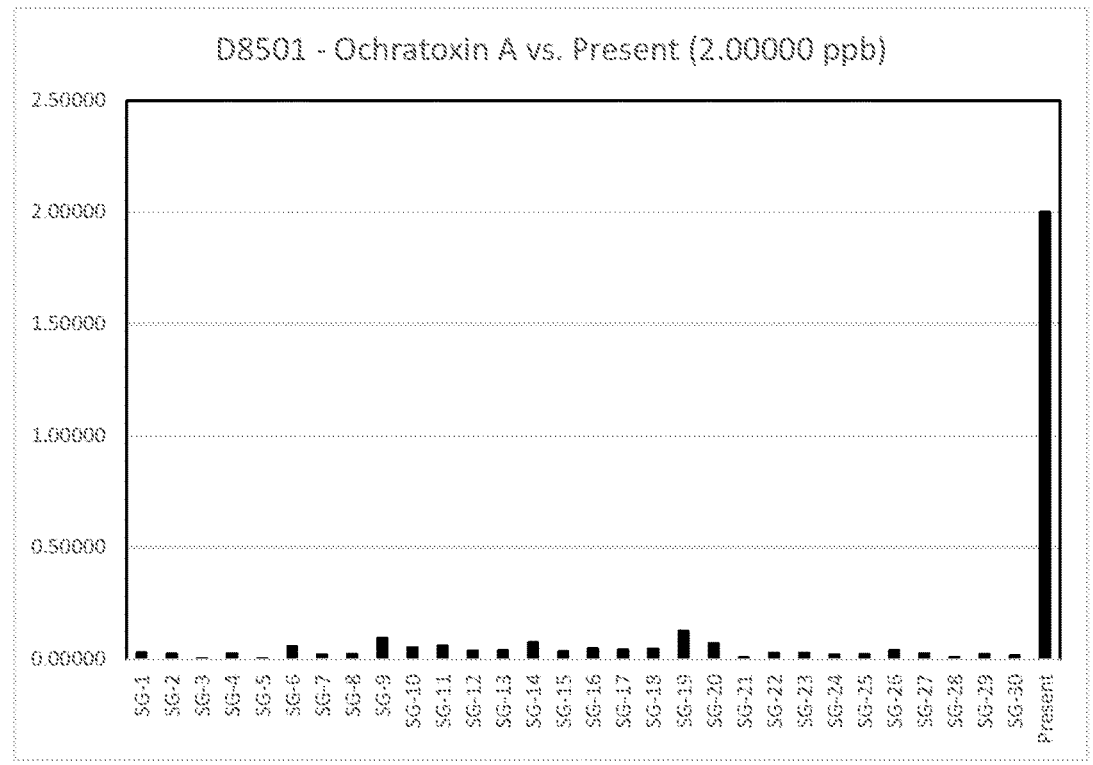
FIG. 2 is a bar graph illustrating the data from Table 7.

See also FIG. 2 graph for illustration.

TABLE 8

D8502 - Aflatoxin Group

| Test Date | Sample | ppb |
|---|---|---|
| Day 0 | #1 | 2.03000 |
| Day 0 | #2 | 2.14300 |
| Day 0 | #3 | 299.10000 |
| Day 1 | SG-1 | 0.10100 |
| Day 1 | SG-2 | 0.09600 |
| Day 1 | SG-3 | 0.08000 |
| Day 1 | SG-4 | 0.14700 |
| Day 1 | SG-5 | 0.09200 |
| Day 30 | SG-6 | 0.10600 |
| Day 30 | SG-7 | 0.06100 |
| Day 30 | SG-8 | 0.06100 |
| Day 30 | SG-9 | 0.12000 |
| Day 30 | SG-10 | 0.10700 |
| Day 90 | SG-11 | 0.14100 |
| Day 90 | SG-12 | 0.08200 |
| Day 90 | SG-13 | 0.08700 |
| Day 90 | SG-14 | 0.11900 |
| Day 90 | SG-15 | 0.09500 |
| Day 180 | SG-16 | 0.04000 |
| Day 180 | SG-17 | 0.07000 |
| Day 180 | SG-18 | 0.07400 |
| Day 180 | SG-19 | 0.10700 |
| Day 180 | SG-20 | 0.01200 |
| Day 270 | SG-21 | 0.06900 |
| Day 270 | SG-22 | 0.09000 |
| Day 270 | SG-23 | 0.07900 |
| Day 270 | SG-24 | 0.10600 |
| Day 270 | SG-25 | 0.07100 |
| Day 365 | SG-26 | 0.09400 |
| Day 365 | SG-27 | 0.13100 |
| Day 365 | SG-28 | 0.16100 |
| Day 365 | SG-29 | 0.07900 |
| Day 365 | SG-30 | 0.09300 |

Figure 3:
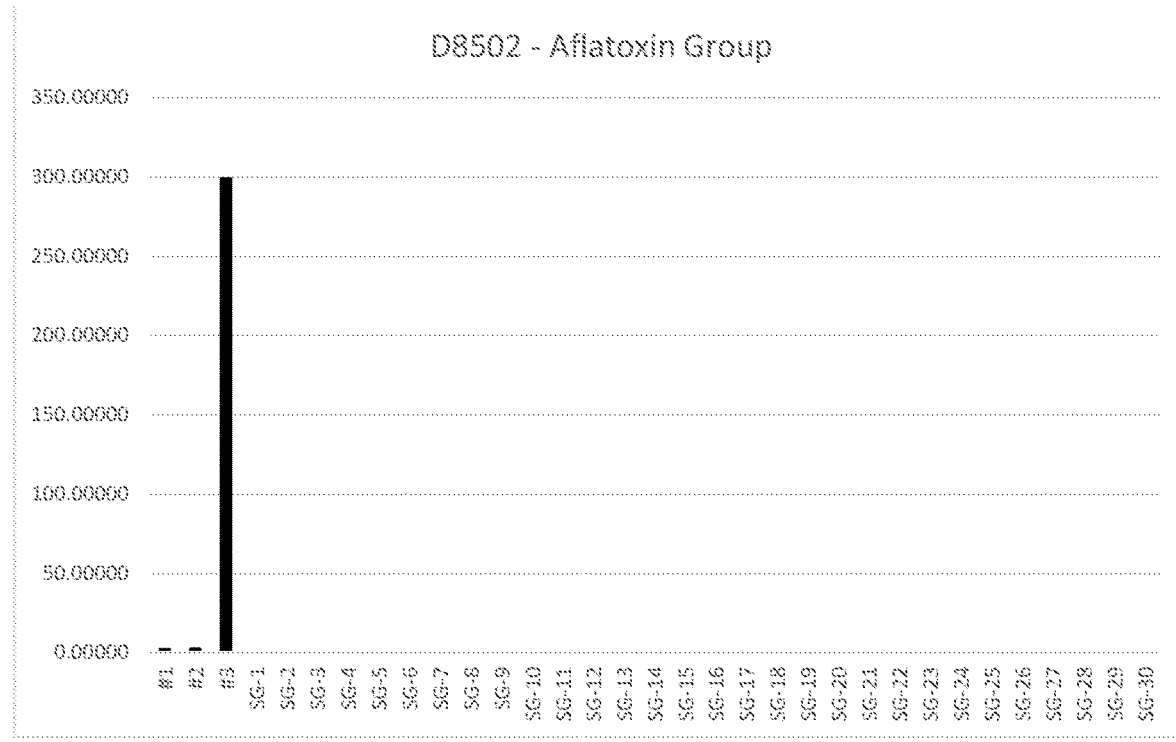
FIG. 3 is a bar graph illustrating the data from Table 8.

See also FIG. 3 graph for illustration.

TABLE 9

D8502 - Aflatoxin Group

| Test Date | Sample | ppb |
|---|---|---|
| Day 1 | SG-1 | 0.10100 |
| Day 1 | SG-2 | 0.09600 |
| Day 1 | SG-3 | 0.08000 |
| Day 1 | SG-4 | 0.14700 |
| Day 1 | SG-5 | 0.09200 |
| Day 30 | SG-6 | 0.10600 |
| Day 30 | SG-7 | 0.06100 |
| Day 30 | SG-8 | 0.06100 |
| Day 30 | SG-9 | 0.12000 |
| Day 30 | SG-10 | 0.10700 |
| Day 90 | SG-11 | 0.14100 |
| Day 90 | SG-12 | 0.08200 |
| Day 90 | SG-13 | 0.08700 |
| Day 90 | SG-14 | 0.11900 |
| Day 90 | SG-15 | 0.09500 |
| Day 180 | SG-16 | 0.04000 |
| Day 180 | SG-17 | 0.07000 |
| Day 180 | SG-18 | 0.07400 |
| Day 180 | SG-19 | 0.10700 |
| Day 180 | SG-20 | 0.01200 |
| Day 270 | SG-21 | 0.06900 |
| Day 270 | SG-22 | 0.09000 |
| Day 270 | SG-23 | 0.07900 |
| Day 270 | SG-24 | 0.10600 |
| Day 270 | SG-25 | 0.07100 |
| Day 365 | SG-26 | 0.09400 |
| Day 365 | SG-27 | 0.13100 |
| Day 365 | SG-28 | 0.16100 |
| Day 365 | SG-29 | 0.07900 |
| Day 365 | SG-30 | 0.09300 |
| Defined | Present | 1.00000 |

Figure 4:
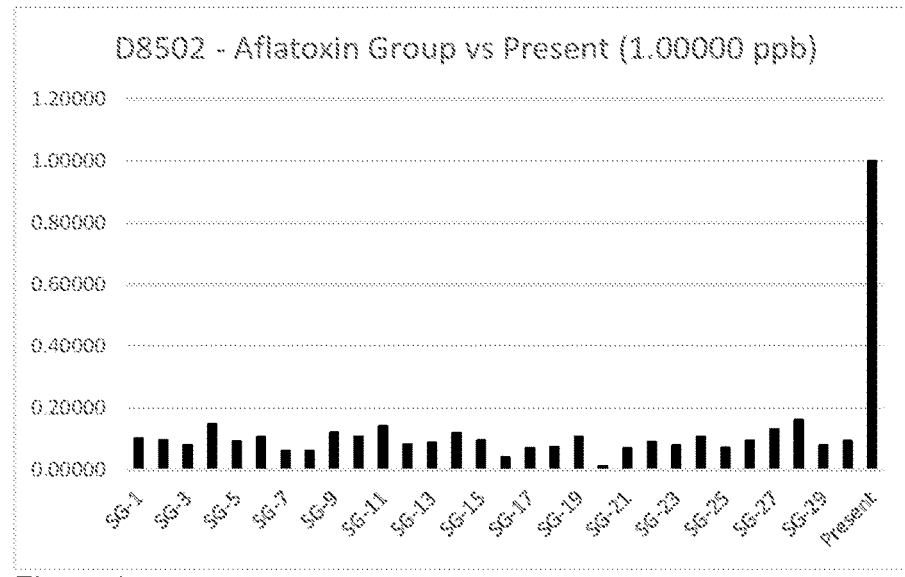
FIG. 4 is a bar graph illustrating the data from Table 9.

See also FIG. 4 graph for illustration.

TABLE 10

D8503 - Tricothecene Group

| Test Date | Sample | ppb |
|---|---|---|
| Day 0 | #1 | 0.59500 |
| Day 0 | #2 | 0.36900 |
| Day 0 | #3 | 0.16100 |
| Day 1 | SG-1 | 0.00000 |
| Day 1 | SG-2 | 0.00000 |
| Day 1 | SG-3 | 0.00000 |
| Day 1 | SG-4 | 0.00000 |
| Day 1 | SG-5 | 0.00000 |
| Day 30 | SG-6 | 0.00000 |
| Day 30 | SG-7 | 0.00000 |
| Day 30 | SG-8 | 0.00100 |
| Day 30 | SG-9 | 0.00100 |
| Day 30 | SG-10 | 0.00100 |
| Day 90 | SG-11 | 0.00100 |
| Day 90 | SG-12 | 0.00100 |
| Day 90 | SG-13 | 0.00100 |
| Day 90 | SG-14 | 0.00100 |
| Day 90 | SG-15 | 0.00100 |
| Day 180 | SG-16 | 0.00000 |
| Day 180 | SG-17 | 0.00000 |
| Day 180 | SG-18 | 0.00100 |
| Day 180 | SG-19 | 0.00200 |
| Day 180 | SG-20 | 0.00000 |
| Day 270 | SG-21 | 0.00000 |
| Day 270 | SG-22 | 0.00000 |
| Day 270 | SG-23 | 0.00000 |
| Day 270 | SG-24 | 0.00000 |
| Day 270 | SG-25 | 0.00000 |
| Day 365 | SG-26 | 0.00100 |
| Day 365 | SG-27 | 0.00900 |
| Day 365 | SG-28 | 0.00200 |
| Day 365 | SG-29 | 0.00100 |
| Day 365 | SG-30 | 0.00400 |

Figure 5:
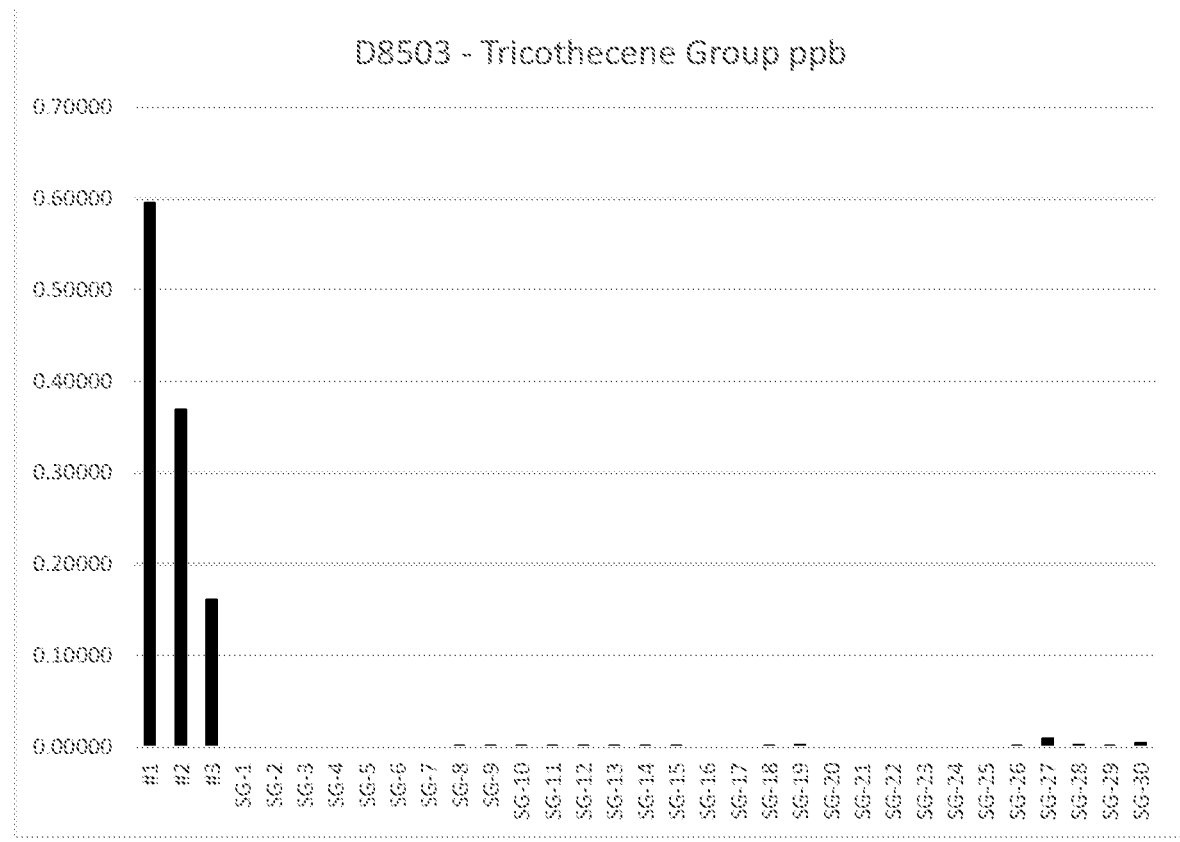
FIG. 5 is a bar graph illustrating the data from Table 10.

See also FIG. 5 graph for illustration.

TABLE 11

D8503 - Tricothecene Group

| Test Date | Sample | ppb |
|---|---|---|
| Day 1 | SG-1 | 0.00000 |
| Day 1 | SG-2 | 0.00000 |
| Day 1 | SG-3 | 0.00000 |
| Day 1 | SG-4 | 0.00000 |
| Day 1 | SG-5 | 0.00000 |
| Day 30 | SG-6 | 0.00000 |
| Day 30 | SG-7 | 0.00000 |
| Day 30 | SG-8 | 0.00100 |
| Day 30 | SG-9 | 0.00100 |
| Day 30 | SG-10 | 0.00100 |
| Day 90 | SG-11 | 0.00100 |
| Day 90 | SG-12 | 0.00100 |
| Day 90 | SG-13 | 0.00100 |
| Day 90 | SG-14 | 0.00100 |
| Day 90 | SG-15 | 0.00100 |
| Day 180 | SG-16 | 0.00000 |
| Day 180 | SG-17 | 0.00000 |

TABLE 11-continued

D8503 - Tricothecene Group

| Test Date | Sample | ppb |
|---|---|---|
| Day 180 | SG-18 | 0.00100 |
| Day 180 | SG-19 | 0.00200 |
| Day 180 | SG-20 | 0.00000 |
| Day 270 | SG-21 | 0.00000 |
| Day 270 | SG-22 | 0.00000 |
| Day 270 | SG-23 | 0.00000 |
| Day 270 | SG-24 | 0.00000 |
| Day 270 | SG-25 | 0.00000 |
| Day 365 | SG-26 | 0.00100 |
| Day 365 | SG-27 | 0.09900 |
| Day 365 | SG-28 | 0.00200 |
| Day 365 | SG-29 | 0.00100 |
| Day 365 | SG-30 | 0.00400 |
| Defined | Present | 0.03000 |

Figure 6:
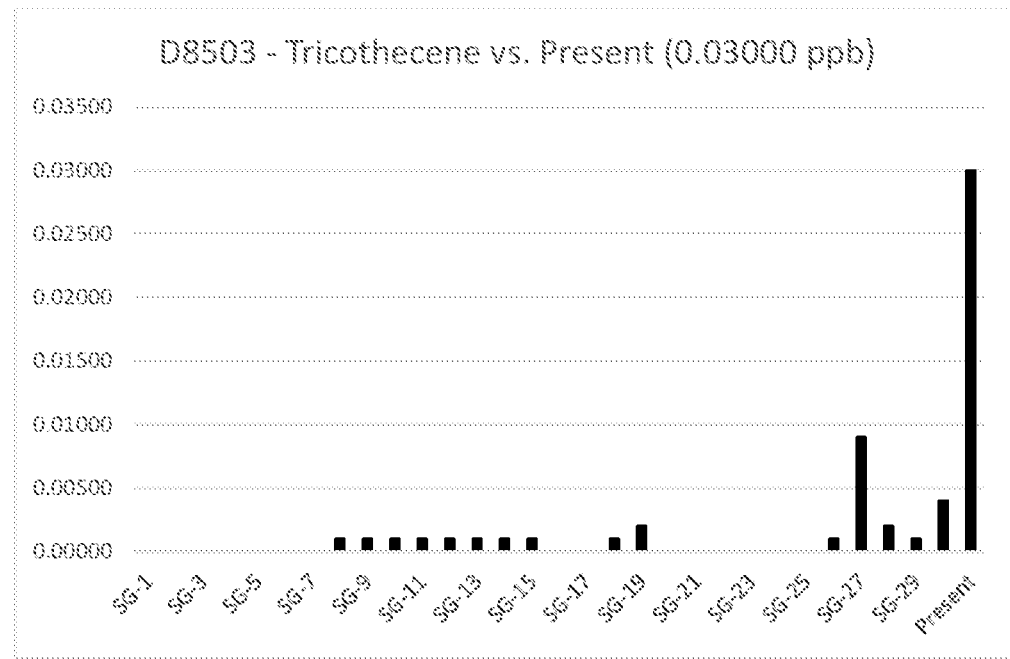
FIG. 6 is a bar graph illustrating the data from Table 11.

See also FIG. 6 graph for illustration.

TABLE 12

D8510 - Gliotoxin Derivative

| Test Date | Sample | ppb |
|---|---|---|
| Day 0 | #1 | 7.43500 |
| Day 0 | #2 | 5.02500 |
| Day 0 | #3 | 2.69700 |
| Day 1 | SG-1 | 0.00000 |
| Day 1 | SG-2 | 0.00000 |
| Day 1 | SG-3 | 0.00000 |
| Day 1 | SG-4 | 0.00000 |
| Day 1 | SG-5 | 0.00000 |
| Day 30 | SG-6 | 0.00000 |
| Day 30 | SG-7 | 0.00000 |
| Day 30 | SG-8 | 0.00000 |
| Day 30 | SG-9 | 0.00000 |
| Day 30 | SG-10 | 0.00000 |
| Day 90 | SG-11 | 0.00000 |
| Day 90 | SG-12 | 0.00000 |
| Day 90 | SG-13 | 0.00000 |
| Day 90 | SG-14 | 0.00000 |
| Day 90 | SG-15 | 0.00000 |
| Day 180 | SG-16 | 0.00000 |
| Day 180 | SG-17 | 0.00000 |
| Day 180 | SG-18 | 0.00000 |
| Day 180 | SG-19 | 0.01800 |
| Day 180 | SG-20 | 0.00000 |
| Day 270 | SG-21 | 0.00100 |
| Day 270 | SG-22 | 0.00000 |
| Day 270 | SG-23 | 0.00000 |
| Day 270 | SG-24 | 0.00000 |

TABLE 12-continued

D8510 - Gliotoxin Derivative

| Test Date | Sample | ppb |
|---|---|---|
| Day 270 | SG-25 | 0.00000 |
| Day 365 | SG-26 | 0.00000 |
| Day 365 | SG-27 | 0.00000 |
| Day 365 | SG-28 | 0.00000 |
| Day 365 | SG-29 | 0.00000 |
| Day 365 | SG-30 | 0.00000 |

Figure 7:
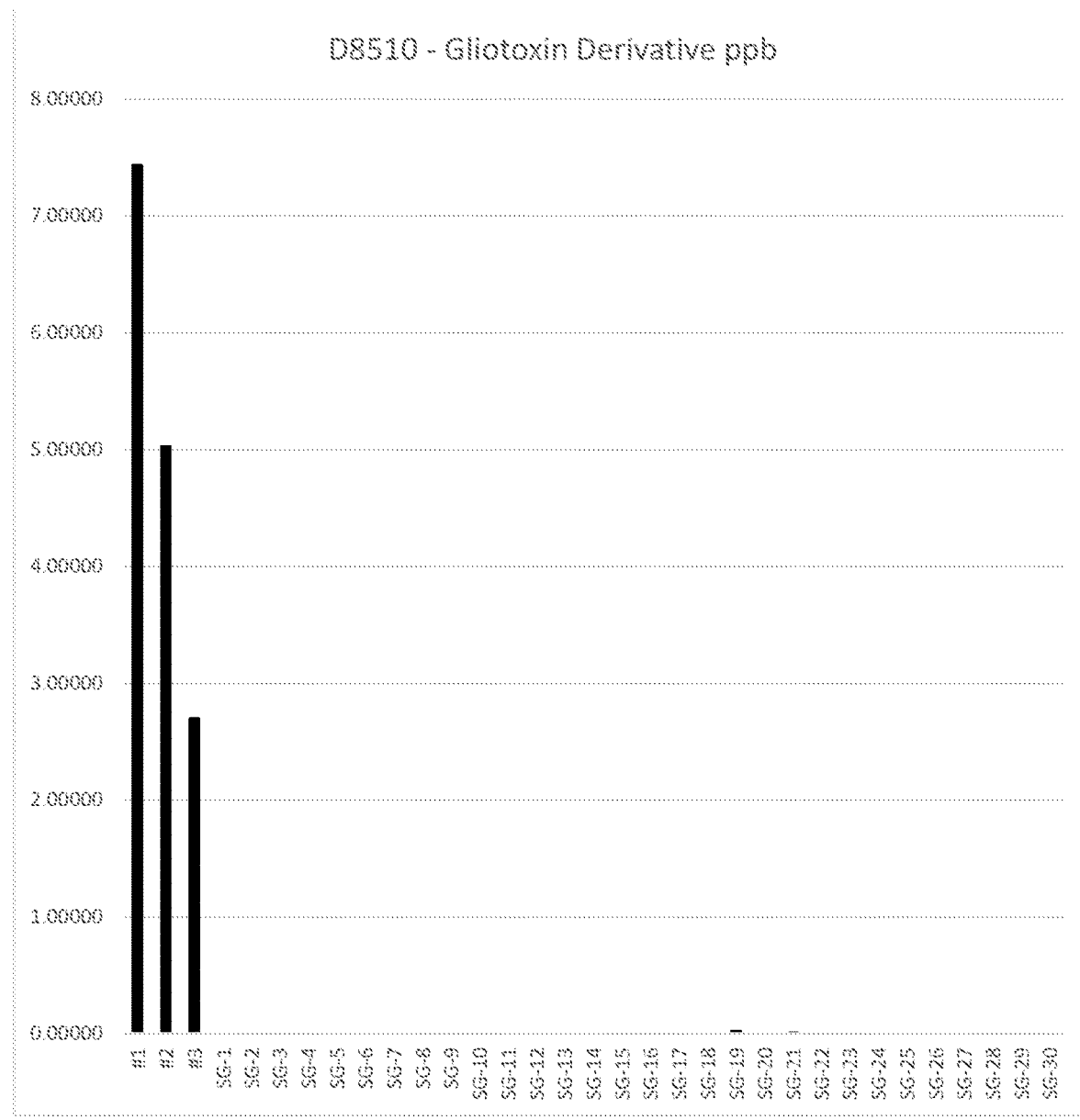
FIG. 7 is a bar graph illustrating the data from Table 12.

See also FIG. 7 graph for illustration.

TABLE 13

D8510 - Gliotoxin Derivative

| Test Date | Sample | ppb |
|---|---|---|
| Day 1 | SG-1 | 0.00000 |
| Day 1 | SG-2 | 0.00000 |
| Day 1 | SG-3 | 0.00000 |
| Day 1 | SG-4 | 0.00000 |
| Day 1 | SG-5 | 0.00000 |
| Day 30 | SG-6 | 0.00000 |
| Day 30 | SG-7 | 0.00000 |
| Day 30 | SG-8 | 0.00000 |
| Day 30 | SG-9 | 0.00000 |
| Day 30 | SG-10 | 0.00000 |
| Day 90 | SG-11 | 0.00000 |
| Day 90 | SG-12 | 0.00000 |
| Day 90 | SG-13 | 0.00000 |
| Day 90 | SG-14 | 0.00000 |
| Day 90 | SG-15 | 0.00000 |
| Day 180 | SG-16 | 0.00000 |
| Day 180 | SG-17 | 0.00000 |
| Day 180 | SG-18 | 0.00000 |
| Day 180 | SG-19 | 0.01800 |
| Day 180 | SG-20 | 0.00000 |
| Day 270 | SG-21 | 0.00100 |
| Day 270 | SG-22 | 0.00000 |
| Day 270 | SG-23 | 0.00000 |
| Day 270 | SG-24 | 0.00000 |
| Day 270 | SG-25 | 0.00000 |
| Day 365 | SG-26 | 0.00000 |
| Day 365 | SG-27 | 0.00000 |
| Day 365 | SG-28 | 0.00000 |
| Day 365 | SG-29 | 0.00000 |
| Day 365 | SG-30 | 0.00000 |
| Defined | Present | 1.00000 |

Figure 8:
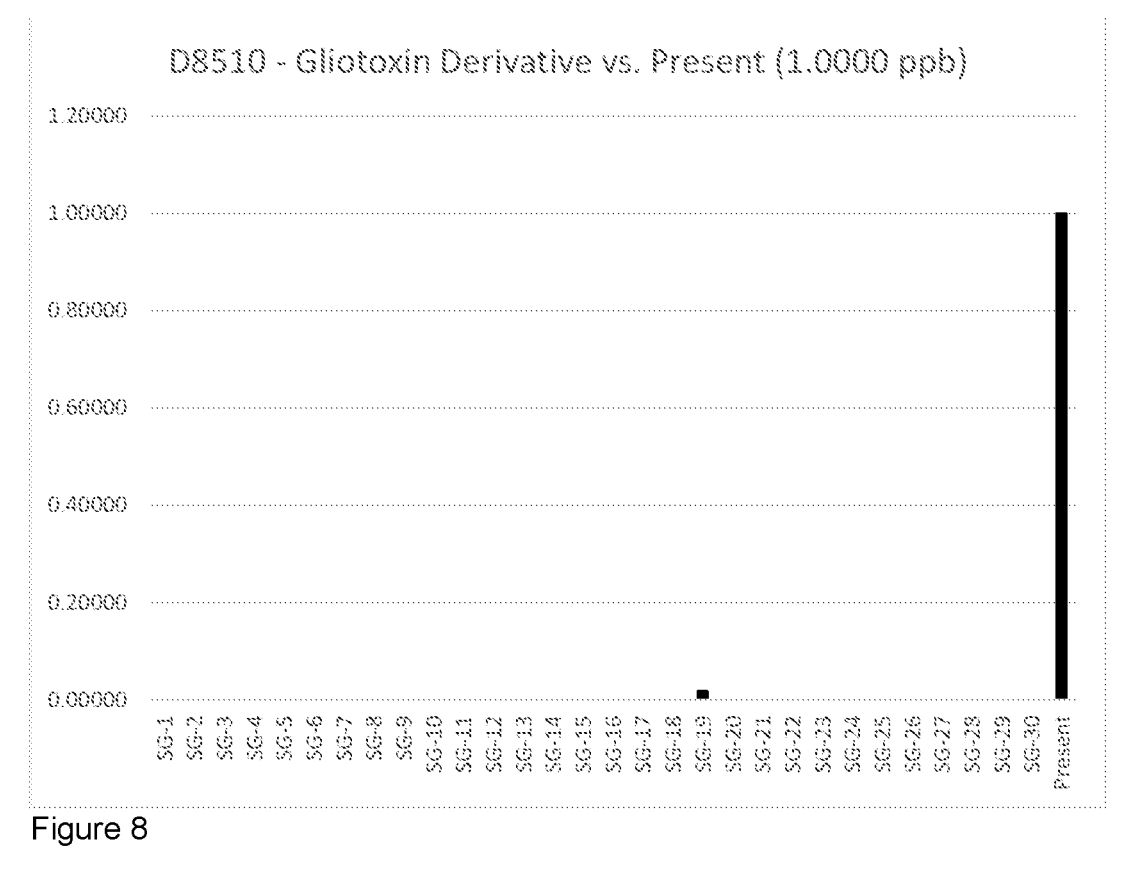

See also FIG. 8 graph for illustration.

Tables 14 through 19 break out the data from Tables 6 through 13.

TABLE 14

To follow is the data collected AFTER GAUZE INOCULATION with MOLD CLEANER

Date of Testing: DAY ONE Nov. 16, 2018

| Project | Accession No. | Date of Service | Date of Receipt | Date of Report | Specimen | | D8501 | D8502 | D8503 | D8510 |
|---|---|---|---|---|---|---|---|---|---|---|
| SG-1 | EN228263 | Apr. 28, 2019 | Apr. 29, 2019 | Apr. 30, 2019 | Dust SG-1 | RESULTS: | 0.03000 Not Present | 0.10100 Not Present | 0.00000 Not Present | 0.00000 Not Present |
| SG-2 | EN228264 | Apr. 28, 2019 | Apr. 29, 2019 | Apr. 30, 2019 | Dust SG-2 | RESULTS: | 0.02500 Not Present | 0.09600 Not Present | 0.00000 Not Present | 0.00000 Not Present |
| SG-3 | EN228265 | Apr. 28, 2019 | Apr. 29, 2019 | Apr. 30, 2019 | Dust SG-3 | RESULTS: | 0.00500 Not Present | 0.08000 Not Present | 0.00000 Not Present | 0.00000 Not Present |

TABLE 14-continued

To follow is the data collected AFTER GAUZE INOCULATION with MOLD CLEANER

Date of Testing: DAY ONE Nov. 16, 2018

| Project: | Accession No.: | Date of Service: | Date of Receipt: | Date of Report: | Specimen: | Value (ppb): D8501 | D8502 | D8503 | D8510 |
|---|---|---|---|---|---|---|---|---|---|
| SG-4 | EN228266 | Apr. 28, 2019 | Apr. 29, 2019 | Apr. 30, 2019 | Dust SG-4 RESULTS: | 0.02600 Not Present | 0.14700 Not Present | 0.00000 Not Present | 0.00000 Not Present |
| SG-5 | EN228267 | Apr. 28, 2019 | Apr. 29, 2019 | Apr. 30, 2019 | Dust SG-5 RESULTS: | 0.00500 Not Present | 0.09200 Not Present | 0.00000 Not Present | 0.00000 Not Present |

TABLE 15

Date of Testing: 30 DAYS - Dec. 16, 2018

| Project: | Accession No.: | Date of Service: | Date of Receipt: | Date of Report: | Specimen: | Value (ppb): D8501 | D8502 | D8503 | D8510 |
|---|---|---|---|---|---|---|---|---|---|
| SG-6 | EN228268 | Apr. 28, 2019 | Apr. 29, 2019 | Apr. 30, 2019 | Dust SG-6 RESULTS: | 0.05800 Not Present | 0.10600 Not Present | 0.00000 Not Present | 0.00000 Not Present |
| SG-7 | EN228269 | Apr. 28, 2019 | Apr. 29, 2019 | Apr. 30, 2019 | Dust SG-7 RESULTS: | 0.02000 Not Present | 0.06100 Not Present | 0.00000 Not Present | 0.00000 Not Present |
| SG-8 | EN228270 | Apr. 28, 2019 | Apr. 29, 2019 | Apr. 30, 2019 | Dust SG-8 RESULTS: | 0.02300 Not Present | 0.06100 Not Present | 0.00100 Not Present | 0.00000 Not Present |
| SG-9 | EN228271 | Apr. 28, 2019 | Apr. 29, 2019 | Apr. 30, 2019 | Dust SG-9 RESULTS: | 0.09400 Not Present | 0.12000 Not Present | 0.00100 Not Present | 0.00000 Not Present |
| SG-10 | EN228272 | Apr. 28, 2019 | Apr. 29, 2019 | Apr. 30, 2019 | Dust SG-10 RESULTS: | 0.05300 Not Present | 0.10700 Not Present | 0.00100 Not Present | 0.00000 Not Present |

TABLE 16

Date of Testing: 90 DAYS - Feb. 16, 2019

| Project: | Accession No.: | Date of Service: | Date of Receipt: | Date of Report: | Specimen: | Value (ppb): D8501 | D8502 | D8503 | D8510 |
|---|---|---|---|---|---|---|---|---|---|
| SG-11 | EN228273 | Apr. 28, 2019 | Apr. 29, 2019 | Apr. 30, 2019 | Dust SG-11 RESULTS: | 0.06000 Not Present | 0.14100 Not Present | 0.00100 Not Present | 0.00000 Not Present |
| SG-12 | EN228274 | Apr. 28, 2019 | Apr. 29, 2019 | Apr. 30, 2019 | Dust SG-12 RESULTS: | 0.03900 Not Present | 0.08200 Not Present | 0.00100 Not Present | 0.00000 Not Present |
| SG-13 | EN228275 | Apr. 28, 2019 | Apr. 29, 2019 | Apr. 30, 2019 | Dust SG-13 RESULTS: | 0.04000 Not Present | 0.08700 Not Present | 0.00100 Not Present | 0.00000 Not Present |
| SG-14 | EN228276 | Apr. 28, 2019 | Apr. 29, 2019 | Apr. 30, 2019 | Dust SG-14 RESULTS: | 0.07600 Not Present | 0.11900 Not Present | 0.00100 Not Present | 0.00000 Not Present |

TABLE 16-continued

| | | Date of Testing: 90 DAYS - Feb. 16, 2019 | | | | | | | |
|---|---|---|---|---|---|---|---|---|---|
| | Accession | Date of | Date of | Date of | | Value (ppb): | | | |
| Project: | No.: | Service: | Receipt: | Report: | Specimen: | D8501 | D8502 | D8503 | D8510 |
| SG-15 | EN228277 | Apr. 28, 2019 | Apr. 29, 2019 | Apr. 30, 2019 | Dust SG-15 RESULTS: | 0.03500 Not Present | 0.09500 Not Present | 0.00100 Not Present | 0.00000 Not Present |

TABLE 17

| | | Date of Testing: 180 DAYS - May 16, 2019 | | | | | | | |
|---|---|---|---|---|---|---|---|---|---|
| | Accession | Date of | Date of | Date of | | Value (ppb): | | | |
| Project: | No.: | Service: | Receipt: | Report: | Specimen: | D8501 | D8502 | D8503 | D8510 |
| SG-16 | EN232379 | May 16, 2019 | Oct. 7, 2019 | Oct. 8, 2019 | Dust SG-16 RESULTS: | 0.04900 Not Present | 0.04000 Not Present | 0.00000 Not Present | 0.00000 Not Present |
| SG-17 | EN232381 | May 16, 2019 | Oct. 7, 2019 | Oct. 8, 2019 | Dust SG-17 RESULTS: | 0.04300 Not Present | 0.07000 Not Present | 0.00000 Not Present | 0.00000 Not Present |
| SG-18 | EN232380 | May 16, 2019 | Oct. 7, 2019 | Oct. 8, 2019 | Dust SG-18 RESULTS: | 0.04700 Not Present | 0.07400 Not Present | 0.00100 Not Present | 0.00000 Not Present |
| SG-19 | EN232389 | May 16, 2019 | Oct. 7, 2019 | Oct. 8, 2019 | Dust SG-19 SG-19 RESULTS: | 0.12600 Not Present | 0.10700 Not Present | 0.00200 Not Present | 0.01800 Not Present |
| SG-20 | EN232388 | May 16, 2019 | Oct. 7, 2019 | Oct. 8, 2019 | Dust SG-20 RESULTS: | 0.07200 Not Present | 0.01200 Not Present | 0.00000 Not Present | 0.00000 Not Present |

TABLE 18

| | | Date of Testing: 270 DAYS - Aug. 16, 2019 | | | | | | | |
|---|---|---|---|---|---|---|---|---|---|
| | Accession | Date of | Date of | Date of | | Value (ppb): | | | |
| Project: | No.: | Service: | Receipt: | Report: | Specimen: | D8501 | D8502 | D8503 | D8510 |
| SG-21 | EN232387 | May 16, 2019 | Oct. 7, 2019 | Oct. 8, 2019 | Dust SG-21 RESULTS: | 0.00800 Not Present | 0.06900 Not Present | 0.00000 Not Present | 0.00100 Not Present |
| SG-22 | EN232386 | May 16, 2019 | Oct. 7, 2019 | Oct. 8, 2019 | Dust SG-22 RESULTS: | 0.02900 Not Present | 0.09000 Not Present | 0.00000 Not Present | 0.00000 Not Present |
| SG-23 | EN232385 | May 16, 2019 | Oct. 7, 2019 | Oct. 8, 2019 | Dust SG-23 RESULTS: | 0.02900 Not Present | 0.07900 Not Present | 0.00000 Not Present | 0.00000 Not Present |
| SG-24 | EN232384 | May 16, 2019 | Oct. 7, 2019 | Oct. 8, 2019 | Dust SG-24 RESULTS: | 0.02100 Not Present | 0.10600 Not Present | 0.00000 Not Present | 0.00000 Not Present |
| SG-25 | EN232383 | May 16, 2019 | Oct. 7, 2019 | Oct. 8, 2019 | Dust SG-25 RESULTS: | 0.02200 Not Present | 0.07100 Not Present | 0.00000 Not Present | 0.00000 Not Present |

TABLE 19

| | | | | | | Value (ppb): | | | |
|---|---|---|---|---|---|---|---|---|---|
| Project: | Accession No.: | Date of Service: | Date of Receipt: | Date of Report: | Specimen: | D8501 | D8502 | D8503 | D8510 |

Date of Testing: 365 DAYS - Nov. 21, 2019

| Project: | Accession No.: | Date of Service: | Date of Receipt: | Date of Report: | Specimen: | D8501 | D8502 | D8503 | D8510 |
|---|---|---|---|---|---|---|---|---|---|
| SG-26 | EN236022 | Nov. 27, 2019 | Nov. 27, 2019 | Dec. 3, 2019 | Dust SG-26 RESULTS: | 0.04000 Not Present | 0.09400 Not Present | 0.00100 Not Present | 0.00000 Not Present |
| SG-27 | EN236023 | Nov. 27, 2019 | Nov. 27, 2019 | Dec. 3, 2019 | Dust SG-27 RESULTS: | 0.02600 Not Present | 0.13100 Not Present | 0.00900 Not Present | 0.00000 Not Present |
| SG-28 | EN236023 | Nov. 27, 2019 | Nov. 27, 2019 | Dec. 3, 2019 | Dust SG-28 RESULTS: | 0.01000 Not Present | 0.16100 Not Present | 0.00200 Not Present | 0.00000 Not Present |
| SG-29 | EN236025 | Nov. 27, 2019 | Nov. 27, 2019 | Dec. 3, 2019 | Dust SG-29 RESULTS: | 0.02300 Not Present | 0.07900 Not Present | 0.00100 Not Present | 0.00000 Not Present |
| SG-30 | EN236026 | Nov. 27, 2019 | Nov. 27, 2019 | Dec. 3, 2019 | Dust SG-30 RESULTS: | 0.01600 Not Present | 0.09300 Not Present | 0.00400 Not Present | 0.00000 Not Present |

Summary and Discussion:

Results of a one-year study of FCC and the interactions against 15 mycotoxins and *Candida auris* demonstrated no mycotoxin presence in the same samples after 365 days and no *Candida auris* after the same time period.

This one-year study demonstrates efficacy of the product FCC for mycotoxins at levels of 0-70 ppb (dependent on the mycotoxin studied) used at levels suggested by the manufacturer. The product does modify the mycotoxins in such a way that they are not detected by the ELISA technique. The product also kills the organism, *Candida auris.*

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

The present invention may be embodied in other forms without departing from the spirit and the essential attributes thereof, and, accordingly, reference should be made to the appended claims, rather than to the foregoing specification, as indicating the scope of the invention. The invention illustratively disclosed herein suitably may be practiced in the absence of any element which is not specifically disclosed herein.

The invention claimed is:

1. A method of treating a building for mold contamination consisting of the steps of:
   a. assessing and locating mold growth areas;
   b. constructing a containment barrier around one or more areas to be treated to isolate designated areas from the rest of the structure, if necessary;
   c. installing air scrubbers as needed;
   d. vacuuming, abrading and surface treating exposed framing with visible microbial growth;
   e. surface treating salvageable building materials with mold cleaner;
   f. removing air filters from air handlers and disposing the filters;
   g. removing all registers and vent grills in the treated areas;
   h. washing the vent grills with mold cleaner;
   i. vacuuming all registers and accessible ductwork;
   j. vacuuming the interior of the air handler;
   k. surface treating coils and sheet metal with mold cleaner;
   l. treating the heating and ventilation system and associated ductwork with a mold cleaner;
   m. treating the work area including any exposed wall cavities with a mold cleaner, wherein the mold cleaner includes water, propylene glycol, a combination of enzymes consisting of protease, lipase, and amylase, one or more botanical enzyme products, one or more buffers, one or more surfactants, one or more biocides, one or more terpenes, and citrus based turpine D-Limonene;
   n. vacuuming all flooring;
   o. surface treating the ceilings, walls and window treatments in affected areas with mold cleaner;
   p. treating horizontal hard surfaces with mold cleaner;
   q. vacuuming all horizontal hard surfaces;
   r. vacuuming all walls;
   S. vacuuming all upholstered furniture and mattresses;
   t. vacuuming all flooring a second time;
   u. treating the heating and ventilation system and associated ductwork with a mold cleaner a second time;
   v. treating the work area including any exposed wall cavities with a mold cleaner a second time;
   w. deconstructing the containment barrier;
   x. discarding containment barrier; and
   y. reinstalling all registers and vent grills.

2. The method of claim 1 wherein the vacuum is equipped with an ultra low particulate air (ULPA) filter or similar filter with a minimum particle penetration size of 0.1 μm is used for all vacuuming to ensure the removal of 99.999% of mold, dust, pollen, bacteria and airborne particles.

3. The method of claim 1 wherein the mold cleaner can be a surface mold cleaner enzymatic mold cleaner or similar cleaner.

4. The method of claim 1 wherein the atomized mold cleaner can be an air or airborne mold cleaner enzymatic mold cleaner or similar cleaner.

5. The method of claim 1 wherein the air scrubbers can be high efficiency particulate air (HEPA) filter or similar filter which will remove at least 99.95% of particles whose diameter is equal to 0.3 μm from the air that passes through the filter.

6. The method of claim 1 wherein the method is used to treat a building for any type of fungi.

7. A method of treating a building for mold contamination consisting of the steps of:
    a. assessing and locating mold growth areas;
    b. constructing a containment barrier around one or more areas to be treated to isolate designated areas from the rest of the structure, if necessary;
    C. vacuuming, abrading and surface treating exposed framing with visible microbial growth;
    d. surface treating salvageable building materials with mold cleaner, wherein the mold cleaner consists of water, propylene glycol, a combination of enzymes consisting of protease, lipase, and amylase, one or more botanical enzyme products, one or more buffers, one or more surfactants, one or more biocides, one or more terpenes, and citrus based turpine D-Limonene;
    e. removing air filters from air handlers and disposing the filters;
    f. removing all registers and vent grills in the treated areas;
    g. washing the vent grills with mold cleaner;
    h. vacuuming all registers and accessible ductwork;
    i. vacuuming the interior of the air handler;
    j. surface treating coils and sheet metal with mold cleaner;
    k. treating the heating and ventilation system and associated ductwork with a mold cleaner;
    l. Treating the work area including any exposed wall cavities with a mold cleaner;
    m. vacuuming all flooring;
    n. surface treating the ceilings, walls and window treatments in affected areas with mold cleaner;
    o. treating horizontal hard surfaces with mold cleaner;
    p. vacuuming all horizontal hard surfaces;
    q. vacuuming all walls;
    r. vacuuming all upholstered furniture and mattresses;
    s. deconstructing the containment barrier;
    t. discarding containment barrier; and
    u. reinstalling all registers and vent grills.

8. The method of claim 7 further including the step of installing air scrubbers as needed.

9. The method of claim 7 wherein the vacuum is equipped with an ultra low particulate air (ULPA) filter or similar filter with a minimum particle penetration size of 0.1 μm is used for all vacuuming to ensure the removal of 99.999% of mold, dust, pollen, bacteria and airborne particles.

10. The method of claim 7 wherein the mold cleaner can be a surface mold cleaner enzymatic mold cleaner or similar cleaner.

11. The method of claim 7 wherein the atomized mold cleaner can be an air guard enzymatic mold cleaner or similar cleaner.

12. The method of claim 7 wherein the air scrubbers can be high efficiency particulate air (HEPA) filter or similar filter which will remove at least 99.95% of particles whose diameter is equal to 0.3 μm from the air that passes through the filter.

13. The method of claim 7 further including the step of vacuuming all flooring a second time.

14. The method of claim 7 further including the step of treating the heating and ventilation system and associated ductwork with an atomized mold cleaner a second time.

15. The method of claim 7 further including the step of treating the work area including any exposed wall cavities with an atomized mold cleaner a second time.

16. The method of claim 7 wherein the method is used to treat a building for any type of fungi.

\* \* \* \* \*